(12) United States Patent
Amir

(10) Patent No.: US 10,420,921 B2
(45) Date of Patent: Sep. 24, 2019

(54) DELIVERY DEVICES AND METHODS FOR SKIN AUGMENTATION

(71) Applicant: Avraham Amir, Tel Mond (IL)

(72) Inventor: Avraham Amir, Tel Mond (IL)

(73) Assignee: Avraham Amir, Tel Mond (IL)

( * ) Notice: Subject to any disclaimer, the term of this patent is extended or adjusted under 35 U.S.C. 154(b) by 828 days.

(21) Appl. No.: 14/427,309

(22) PCT Filed: Jun. 13, 2013

(86) PCT No.: PCT/IL2013/050510
§ 371 (c)(1),
(2) Date: Mar. 11, 2015

(87) PCT Pub. No.: WO2014/041531
PCT Pub. Date: Mar. 20, 2014

(65) Prior Publication Data
US 2015/0209563 A1 Jul. 30, 2015

Related U.S. Application Data

(60) Provisional application No. 61/725,498, filed on Nov. 13, 2012, provisional application No. 61/721,037, (Continued)

(51) Int. Cl.
*A61M 37/00* (2006.01)
*A61K 9/00* (2006.01)
(Continued)

(52) U.S. Cl.
CPC .......... *A61M 37/0015* (2013.01); *A61K 8/02* (2013.01); *A61K 8/24* (2013.01); *A61K 8/86* (2013.01);
(Continued)

(58) Field of Classification Search
CPC ................ A61K 9/0021; A61K 8/02; A61M 2037/0023; A61M 2037/0046;
(Continued)

(56) References Cited

U.S. PATENT DOCUMENTS 7,655,250 B2 2/2010 Mansouri
8,167,852 B2 5/2012 Quan
(Continued)

FOREIGN PATENT DOCUMENTS

EP 2338557 6/2011
JP 2003238347 8/2003
(Continued)

OTHER PUBLICATIONS

Fukamizu et al., (2012) Development of a three-microneedle device for hypodermic drug delivery and clinical application. Plast Reconstr Surg 130(2): 451-5.
(Continued)

*Primary Examiner* — Nathan R Price
*Assistant Examiner* — Courtney B Fredrickson
(74) *Attorney, Agent, or Firm* — Mark S. Cohen; Pearl Cohen; Zedek Latzer Baratz LLP

(57) ABSTRACT

The present invention provides, inter-alia, applicators comprising an array of microneedles for administration of a composition comprising a biocompatible ceramic material effective in augmentation of skin. In particular, the applicators and methods of the present invention are aimed at filling the undesired lines, wrinkles, depressed scars and folds of a subject's skin and restoring youthful fullness to the skin.

16 Claims, 14 Drawing Sheets

Related U.S. Application Data filed on Nov. 1, 2012, provisional application No. 61/700,371, filed on Sep. 13, 2012.

(51) Int. Cl.
| | | |
|---|---|---|
| *A61K 8/02* | (2006.01) | |
| *A61K 8/24* | (2006.01) | |
| *A61K 8/86* | (2006.01) | |
| *A61Q 19/00* | (2006.01) | |
| *A61Q 19/08* | (2006.01) | |
| *B65B 3/00* | (2006.01) | |
| *A61K 8/23* | (2006.01) | |

(52) U.S. Cl.
CPC ............ *A61K 9/0021* (2013.01); *A61Q 19/00* (2013.01); *A61Q 19/08* (2013.01); *B65B 3/003* (2013.01); *A61K 8/23* (2013.01); *A61K 2800/87* (2013.01); *A61K 2800/91* (2013.01); *A61M 2037/0023* (2013.01); *A61M 2037/0046* (2013.01); *A61M 2037/0053* (2013.01); *A61M 2037/0061* (2013.01); *A61M 2210/04* (2013.01)

(58) Field of Classification Search
CPC .. A61M 2037/0053; A61M 2037/0061; A61M 2210/04; A61M 37/0015; A61M 2037/0038
See application file for complete search history.

(56) References Cited

U.S. PATENT DOCUMENTS

| | | | | |
|---|---|---|---|---|
| 2006/0177494 | A1* | 8/2006 | Cormier | A61K 9/0021 424/449 |
| 2007/0224252 | A1* | 9/2007 | Trautman | A61M 37/0015 424/449 |
| 2008/0213461 | A1 | 9/2008 | Gill | |
| 2008/0262444 | A1 | 10/2008 | Takada | |
| 2010/0221314 | A1 | 9/2010 | Matsudo | |
| 2011/0125288 | A1 | 5/2011 | Hubbard | |
| 2012/0265145 | A1 | 10/2012 | Mefti | |
| 2014/0005606 | A1* | 1/2014 | Chen | A61K 9/0021 604/173 |
| 2014/0066842 | A1* | 3/2014 | Zhang | A61K 9/0021 604/46 |
| 2015/0088050 | A1* | 3/2015 | Chang | A61N 1/328 604/20 |
| 2015/0094648 | A1* | 4/2015 | Toyohara | A61K 9/0021 604/46 |

FOREIGN PATENT DOCUMENTS

| | | |
|---|---|---|
| JP | 2008079919 | 4/2008 |
| JP | 2010017214 | 1/2010 |
| JP | 2010502268 | 1/2010 |
| WO | 93/16657 | 9/1993 |
| WO | 01/91846 | 12/2001 |
| WO | 03/092785 | 11/2003 |
| WO | 2008/072229 | 6/2008 |
| WO | WO 2010/071918 | 7/2010 |
| WO | 2011/044367 | 4/2011 |
| WO | 2011/115272 | 9/2011 |

OTHER PUBLICATIONS

Jacovella (2008) Use of calcium hydroxylapatite (Radiesse) for facial augmentation. Clin Interv Aging 3(1): 161-74.

Kim et al., (2012) Microneedles for drug and vaccine delivery. Adv Drug Deliv Rev 64(14): 1547-68.

Nordquist et al., (2007) Novel microneedle patches for active insulin delivery are efficient in maintaining glycaemic control: an initial comparison with subcutaneous administration. Pharm Res 24(7): 1381-8.

Prausnitz et al., (2009) Microneedle-based vaccines. Curr Top Microbiol Immunol 333: 369-93.

Shirkhanzadeh (2005) Microneedles coated with porous calcium phosphate ceramics: effective vehicles for transdermal delivery of solid trehalose. J Mater Sci Mater Med 16(1): 37-45.

Suchaneka and Yoshimura (1998) Processing and properties of hydroxyapatite-based biomaterials for use as hard tissue replacement implants. J MaterRes 13(1): 94-117.

\* cited by examiner

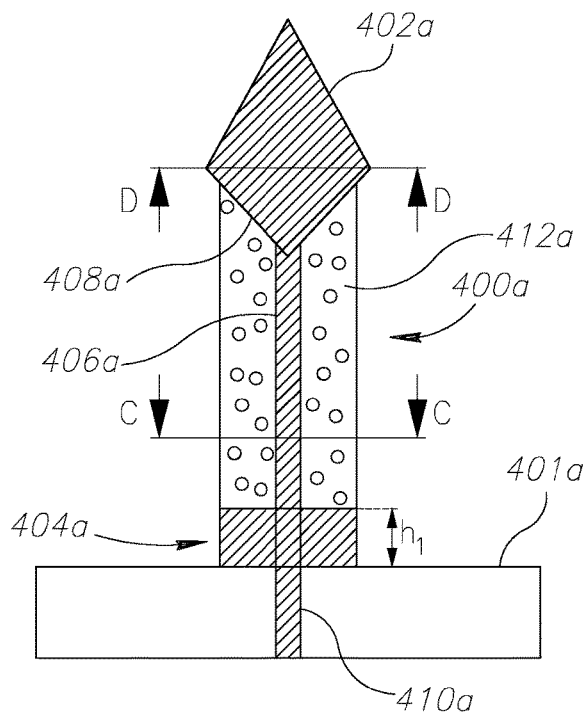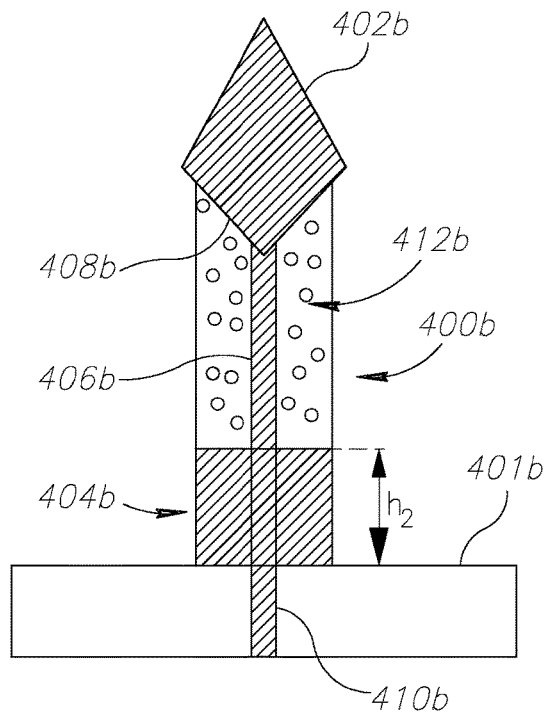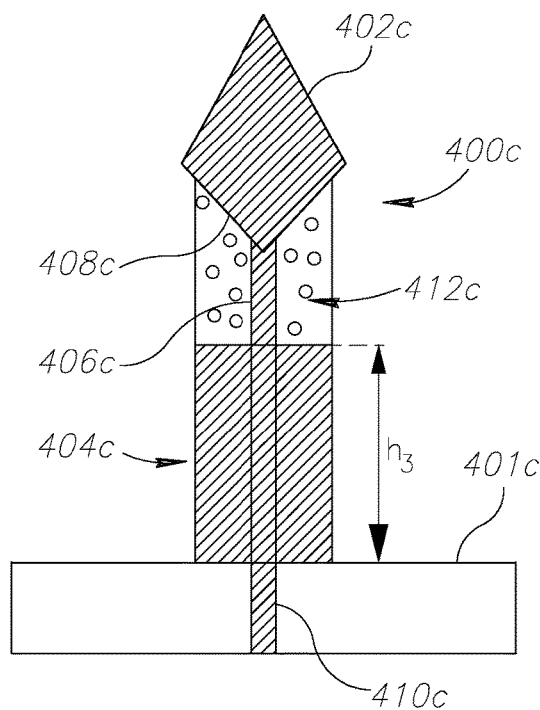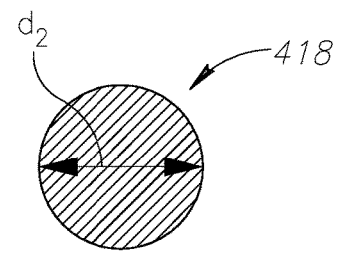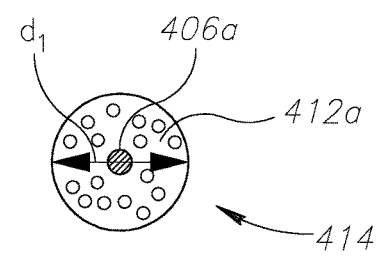
FIG.4A
FIG.4B
FIG.4C
FIG.4E
FIG.4D

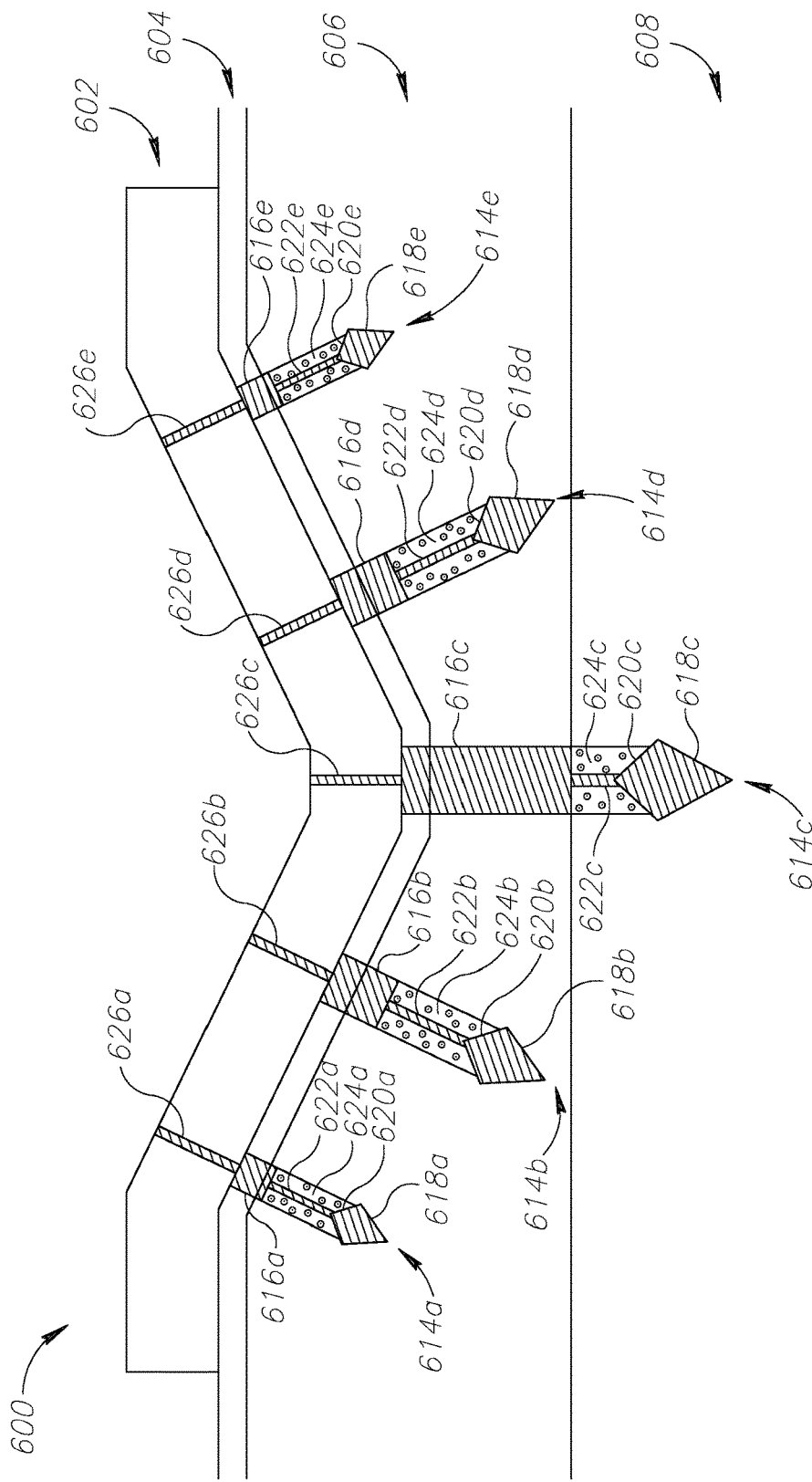

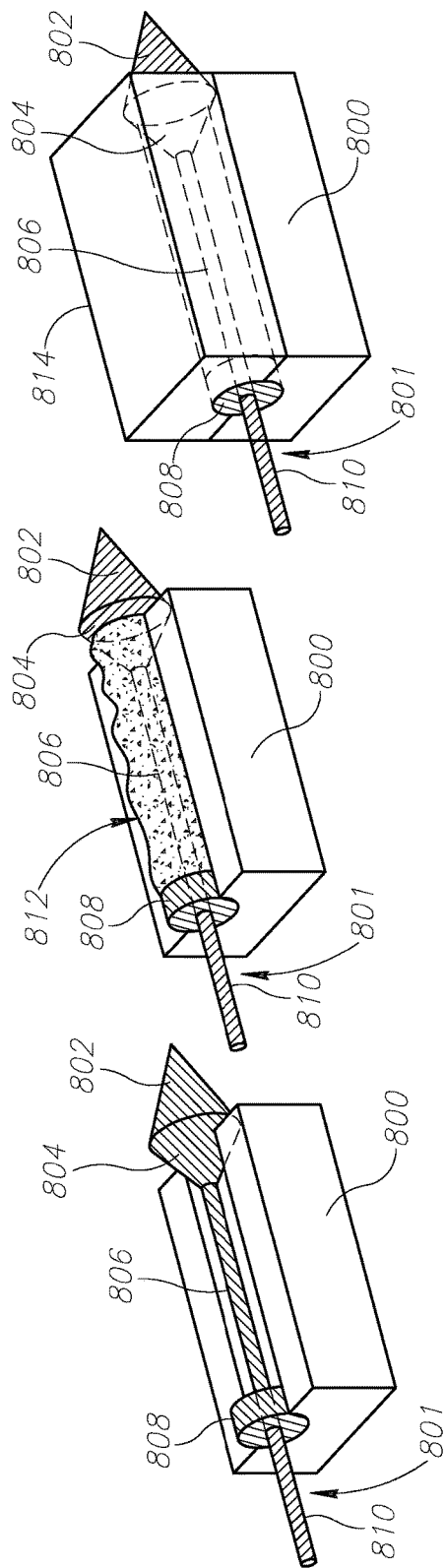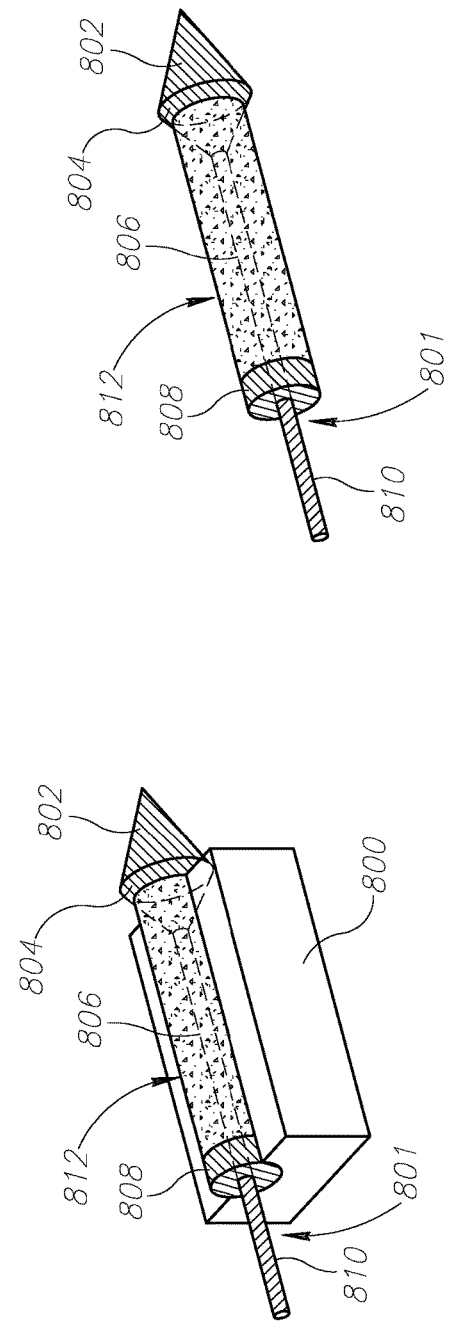

DELIVERY DEVICES AND METHODS FOR SKIN AUGMENTATION

RELATED APPLICATION DATA

This application is the U.S. National Stage of International Application No. PCT/IL2013/050510 filed Jun. 13, 2013, which claims the benefit of United States Provisional Patent Application Nos. 61/725,498 filed Nov. 13, 2012; 61/721,037 filed Nov. 1, 2012; and 61/700,371 filed Sep. 13, 2012. Each of the foregoing applications is hereby incorporated by reference in its entirety for all purposes.

FIELD OF THE INVENTION

The present invention relates to applicators comprising an array of microneedles for the administration of a composition comprising a biocompatible ceramic material effective in augmentation of skin, and methods of use thereof. In particular, the devices and methods of the present invention are aimed at filling the undesired lines, wrinkles, depressed scars and folds of a subject's skin and restoring youthful fullness to the skin.

BACKGROUND OF THE INVENTION

Skin is composed of the epidermis and the dermis. Below these layers lies the hypodermis, which is not usually classified as a layer of skin. The hypodermis is also commonly referred to as subcutaneous fat layer, sub-cutis or subcutaneous tissue. The outermost epidermis is made up of stratified squamous epithelium with an underlying basement membrane. It contains no blood vessels, and is nourished by diffusion from the dermis. The epidermis is mainly composed of keratinocytes, with melanocytes and Langerhans cells also present. This layer of skin functions as a barrier between the body and the external environment, keeping water in the body and preventing penetration of harmful chemicals and pathogens.

The dermis lies below the epidermis and contains a number of structures including blood vessels, nerves, hair follicles, smooth muscle, glands and lymphatic tissue. The dermis (or corium) is typically 0.1-3 mm thick and is the major component of human skin. It is composed of a network of connective tissue, predominantly collagen fibrils providing support and elastin fibers providing flexibility. The main cell types composing the dermis are fibroblasts, adipocytes (fat storage) and macrophages.

The hypodermis lies below the dermis and is important for attaching the skin to the underlying bone and muscle as well as supplying it with blood vessels and nerves. The hypodermis is made up of loose connective tissue and elastin and contains fibroblasts, macrophages and adipocytes. The adipocytes play a major role in the fat storage function of the hypodermis. The fat serves as a filling material and as insulation of the body from the external environment.

Facial aging occurs as the result of several factors, among them are inherent changes within the skin, effects of gravity, activity of facial muscles leading to the formation of dynamic lines, skin loss or shift, bone loss, loss of tissue elasticity and exposure to harsh environmental conditions, particularly the sun or ultraviolet radiation and pollutants. The skin ages when the epidermis begins to thin, causing the junction with the dermis to flatten. Collagen decreases as a person ages and the bundles of collagen, which gives the skin turgor, become looser and lose strength. When the skin loses elasticity, it is less able to resist stretching. Coupled with gravity, muscle pull and tissue changes, the skin begins to wrinkle Water loss and breakdown of bonds between cells also reduces the barrier function of the skin, which can cause the skin's pore size to increase.

There have been efforts to develop and use compositions to correct defects in skin, such as scars and wrinkles, or to augment the tissue of a subject in order to improve the appearance of the skin, particularly facial skin.

Currently, there are dozens of known dermal filling agents for skin augmentation which include autologous implantable materials, allogeneic products, xenogeneic products and synthetically derived products. Available dermal fillers comprise biodegradable natural substances (such as collagen, gelatine, hyaluronic acid, dextran and dried acellular particulate dermal matrix), biodegradable synthetic polymers (such as poly-L-lactic acid, polyethylene oxide and carboxymethylcellulose), non-biodegradable synthetic polymers (such as polymethyl methacrylate, polyacrylamide, polyalkylimide and silicones) and combinations thereof.

Biocompatible ceramic skin augmentation materials, such as hydroxyapatite, are known to be efficient skin augmentation materials due to their properties:

Hydroxyapatite ($Ca_5(PO_4)_3(OH)$) is a naturally occurring mineral form of calcium phosphate. Hydroxyapatite comprises the mineral constituent of bone, therefore rendering it biocompatible and non-immunogenic when introduced into the body of a subject. Of note, Hydroxyapatite is biodegradable following the same metabolic pathways as bone debris resulting from common bone fractures, yet is semi-permanent, as it lasts up to 3 years when implanted into a subject. Moreover, when injected as small microspheres, Hydroxyapatite acts as a scaffold that promotes new tissue formation similar to its surrounding environment. Inside skins such as the dermis, deposited particles of Hydroxyapatite support fibroblastic ingrowth and new collagen formation (Jacovella, P. F, *Clin. Interv. Aging.*, 2008, 3(1): 161-174, Suchanek W. and Yoshimura M., *J. Mater. Res.*, 1997, 13(1): 94-117).

International Publication No. WO/1993/016657 discloses injectable ceramic implant compositions for soft and hard tissue repair and augmentation.

U.S. Pat. No. 7,655,250 discloses a composition for skin application, comprising sintered macroporous hydroxyapatite particles as an absorbance enhancing material.

U.S. Patent Application 2011/0125288 discloses particles of a biocompatible ceramic material in a gel carrier. The biocompatible ceramic material may be hydroxylapatite, polystyrene, polymethylmethacrylate, glass, and stainless steel. Skin augmentation products are typically injected with a needle just below the surface of the skin, at the site of the wrinkle, line, or fold (or scar or subcutaneous tissue to be enhanced). The products essentially plump up the skin from beneath the upper layers of skin. Some skin augmentation products are implanted beneath the skin through an incision. In either case, the skin is cut or punctured with a needle or a scalpel type instrument to insert skin augmentation products into the desired location, and thus the procedure is performed by a trained medical professional. Application of dermal fillers by injection or implantation is uncomfortable and possibly painful to the subject, and, furthermore, requires highly trained medical professional manpower.

International Publication No. WO 2008/072229 discloses a device and methods for delivery of dermal filler compositions into the skin of a subject using a microneedle device.

U.S. Pat. No. 8,167,852 discloses a microneedle device which includes microneedles that can be inserted into skin and dissolve or swell in skin.

It is thus desirable to have highly efficient means for painless self-administration of long lasting skin augmentation products.

SUMMARY OF THE INVENTION

The present invention relates to a device comprising an array of microneedles and a skin augmentation composition useful for augmenting skin in a subject. In particular, the device of the invention is useful for filling undesired lines, wrinkles, depressed scars and folds of a subject's skin. According to the invention, the microneedles advantageously comprise at least one biocompatible ceramic material that is injected into the dermis layer (or lower layers) of a subject's skin and remains there for a prolonged time-period, inducing a filling effect. According to some embodiments, the microneedles comprising the biocompatible ceramic material are propelled into the dermis layer (or lower layers) of a subject's skin. According to some embodiments, only the sharp tip section of each microneedle's skeleton and the middle part of the microneedle, comprising the augmentation composition, are propelled into the dermis layer (or lower layers) of the subject's skin. According to some embodiments, following removal of the microneedles from the subject, the biocompatible ceramic material remains embedded within the treated area for at least several months, preferably more than a year. Each possibility represents a separate embodiment of the present invention.

As used herein, the term "biocompatible ceramic soft-tissue augmentation material", "biocompatible ceramic material" and "biocompatible ceramic" are used interchangeably.

According to some embodiments, the present invention answers the need for devices for self-administration of a skin augmentation composition, that are highly efficient, easy to use, cause minimal discomfort to the treated subject and do not require a trained medical professional. The devices of the invention are able to provide homogenous augmentation of skin lines, wrinkles, depressed scars and folds, thus resulting in a substantially smooth skin surface that may be difficult to obtain through injection or transplantation, especially in fine wrinkles.

According to one aspect, the present invention provides an applicator configured for administration of a skin augmentation composition to a skin and/or sub-cutis of a subject, the applicator comprising a substrate, wherein the substrate has a generally flattened structure having two opposing surfaces, wherein one surface is intended for being placed proximal to the skin of a subject and the other surface facing away from the skin of the subject; and an array of microneedles, wherein the array of microneedles is located on the surface proximal to the skin of the subject, the array comprising a multiplicity of microneedles, wherein each of the microneedles comprises:
  a skeleton made of a rigid material, the skeleton comprises:
    a sharp tip section located on one end of the skeleton, the sharp tip section being configured to penetrate a skin of a subject;
    a base on an opposing end of the skeleton; and
    a middle section connecting between the sharp tip section and the base; and
  a skin augmentation composition comprising at least one biocompatible ceramic material,
  wherein the augmentation composition at least partly surrounds the middle section, such that a diameter of the sharp tip section is larger than a diameter of the augmentation composition.

According to some embodiments, the applicator is configured for administration of a skin augmentation composition to a skin of a subject or to sub-cutis layers of a subject or to a combination thereof. Each possibility represents a separate embodiment of the present invention.

According to another aspect, the present invention provides a microneedle for administration of a skin augmentation composition to a skin and/or sub-cutis of a subject, the microneedle comprising:
  a skeleton made of a rigid material, the skeleton comprises:
    a sharp tip section located on one end of the skeleton, the sharp tip section being configured to penetrate a skin of a subject;
    a base on an opposing end of the skeleton; and
    a middle section connecting between the sharp tip section and the base; and
  a skin augmentation composition comprising at least one biocompatible ceramic material, wherein the augmentation composition at least partly surrounds the middle section, such that a diameter of the sharp tip section is larger than a diameter of the augmentation composition.

According to some embodiments, the microneedle is configured for administration of a skin augmentation composition to a skin of a subject or to sub-cutis layers of a subject or to a combination thereof. Each possibility represents a separate embodiment of the present invention. According to another aspect, the present invention provides a method for filling an undesired fold, wrinkle, line or depressed area in the skin and/or sub-cutis of a subject, comprising placing at the site of the fold, wrinkle, line or depressed area an applicator configured for administration of a skin augmentation composition to a skin and/or sub-cutis of a subject, the applicator comprising a substrate, wherein the substrate has a generally flattened structure having two opposing surfaces, wherein one surface is intended for being placed proximal to the skin of a subject and the other surface facing away from the skin of the subject; and an array of microneedles, wherein the array of microneedles is located on the surface proximal to the skin of the subject, the array comprising a multiplicity of microneedles, wherein each of the microneedles comprises:
  a skeleton made of a rigid material, the skeleton comprises:
    a sharp tip section located on one end of the skeleton, the sharp tip section being configured to penetrate a skin of a subject;
    a base on an opposing end of the skeleton; and
    a middle section connecting between the sharp tip section and the base; and
  a skin augmentation composition comprising at least one biocompatible ceramic material,
  wherein the augmentation composition at least partly surrounds the middle section, such that a diameter of the sharp tip section is larger than a diameter of the augmentation composition.

According to some embodiments, the method of the invention provides filling of an undesired fold, wrinkle, line or depressed area in a skin of a subject or in sub-cutis layers of a subject or in a combination thereof. Each possibility represents a separate embodiment of the present invention.

According to some embodiments, the length of the base is equal or higher than the thickness of the epidermis at a treated area. Each possibility represents a separate embodiment of the present invention. According to some embodiments, the base of the microneedle's skeleton does not comprise the skin augmentation composition. According to some embodiments, a base having a length equal or higher than the thickness of the epidermis at the treated area prevents delivery of the skin augmentation composition to the epidermis. According to some embodiments, the length of the base is variable in correlation to the location in which each microneedle is configured to be situated at within a treated area. It is to be noted that, according to some embodiments, an applicator configured to be placed on a treated area having an epidermis with varying thickness levels may comprise microneedles having bases of varying lengths corresponding to the varying thickness levels. According to some embodiments, the length of the base is variable in correlation to the depth of the skin or subcutaneous layer to be treated by the microneedle. According to some embodiments, microneedles configured to deliver the skin augmentation composition of the invention to a deep skin layer and/or subcutaneously have a longer base than microneedles configured to deliver the composition to a shallower skin layer. According to some embodiments, an applicator configured to deliver the skin augmentation composition of the invention to skin or subcutaneous layers of different depths, comprises microneedles having bases of varying lengths in correlation to the depth of the skin or subcutaneous layer to be treated by each microneedle. Each possibility represents a separate embodiment of the present invention.

According to some embodiments, the present invention provides a method for filling an undesired fold, wrinkle, line or depressed area in a subject, comprising placing the applicator of the invention at the site of the fold, wrinkle, line or depressed area. According to some embodiments, the present invention provides an applicator according to the present invention for use in filling an undesired fold, wrinkle, line or depressed area in the skin of a subject. According to some embodiments, undesired fold, wrinkle, line or depressed area refers to undesired fold, wrinkle, line or depressed area in a skin of a subject or in a sub-cutis of a subject or in a combination thereof. Each possibility represents a separate embodiment of the present invention.

According to some embodiments, the biocompatible ceramic material is a calcium phosphate ceramic material. According to some embodiments, the biocompatible ceramic material is hydroxyapatite. According to some embodiments, the biocompatible ceramic material is biodegradable. According to some embodiment, the biocompatible ceramic material is in the form of particles. According to some embodiment, the biocompatible ceramic material particles are up to a size of 100 micrometers. According to some embodiments, the biocompatible ceramic material particles are of about 10-100 micrometers, preferably of about 40 micrometers. Each possibility represents a separate embodiment of the present invention.

According to some embodiments, the augmentation composition comprises a biodegradable carrier. According to some embodiments, the biodegradable carrier is selected from the group consisting of: a salt, a biodegradable polymer and a combination thereof. According to some embodiments, the biodegradable polymer is a polymer selected from the group consisting of: polyethylene glycol (PEG), Polyglactin 910, Polyglecaprone 25, Polydioxanone, Lactomer 9-1, Glycomer 631, Polyglyconate and a combination thereof. According to some embodiments, the salt is selected from the group consisting of: sodium sulfate, sodium chloride, magnesium sulfate, magnesium citrate, magnesium chloride and a combination thereof. According to some embodiments, the biodegradable carrier comprises magnesium sulfate and polyethylene glycol. According to some embodiments, the augmentation composition comprises hydroxyapatite particles, magnesium sulfate and polyethylene glycol.

According to some embodiments, the augmentation composition comprises at least one type of skin augmentation material. According to various embodiments, the skin augmentation material is selected from the group consisting of: a biodegradable natural substance, a biodegradable synthetic polymer, a non-biodegradable synthetic polymer, a non-biodegradable natural substance and combinations thereof. Each possibility represents a separate embodiment of the present invention.

According to some embodiments, a biodegradable natural substance is selected for example from the group consisting of: bovine collagen, porcine collagen, recombinant collagen, human collagen, gelatin, hyaluronic acid, hyaluronic acid derivative, dried acellular particulate dermal matrix, allogeneic fat and combinations thereof. Each possibility represents a separate embodiment of the present invention.

According to some embodiments, a biodegradable synthetic polymer is selected for example from the group consisting of: poly-L-lactic acid, polyethylene oxide, carboxymethylcellulose and combinations thereof. Each possibility represents a separate embodiment of the present invention.

According to some embodiments, a non-biodegradable synthetic polymer is selected for example from the group consisting of: polymethyl methacrylate, polymethyl methacrylate beads, silicones, silicone rubber, expanded polytetrafluoroethylene, polyacrylamide, polyalkylimide and combinations thereof. Each possibility represents a separate embodiment of the present invention.

According to some embodiments, the augmentation composition further comprises a biologically active agent selected from a group consisting of: an enzyme, a drug, a toxin and a combination thereof. Each possibility represents a separate embodiment of the present invention. According to some embodiments, the toxin is botulinum toxin. According to some embodiments, the toxin is a derivative of botulinum toxin. According to some embodiments, the drug is selected from the group consisting of: an analgesic, a drug for treatment of pathological scarring and a combination thereof. According to some embodiments, the drug is an analgesic. According to some embodiments, the drug for treatment of pathological scarring is a corticosteroid.

According to some embodiments, the augmentation composition further comprises a medical pigment.

According to some embodiments, the substrate is flexible. According to some embodiments, the applicator comprises a plurality of segments, wherein the segments are configured to flexibly move relative to one another. According to some embodiments, each segment comprises a substrate and an array of microneedles. According to some embodiments, the shape of the applicator is adaptable to the outlines of a skin which requires augmentation. According to some embodiments, the substrate is curved.

According to some embodiments, at least a part of each microneedle is substantially composed of the augmentation composition. According to some embodiments, the augmentation composition is within at least a part of each microneedle. According to some embodiments, the microneedles are at least partly coated with the augmentation composition. According to some embodiments, the augmentation composition at least partly surrounds the middle section of the microneedle's skeleton.

According to some embodiments, the rigid material is selected from the group consisting of: metal, plastic, a ceramic material, silicone and a combination thereof. Each possibility represents a separate embodiment of the present invention. According to some embodiments, the rigid material is a metal. According to some embodiments, the metal is selected from the group consisting of: stainless steel, titanium, iron, gold, silver, platinum and a combination thereof. Each possibility represents a separate embodiment of the present invention.

According to some embodiments, the sharp tip section, the base and the middle section of the skeleton are integrally formed. According to some embodiments, the sharp tip section has a shape selected from the group consisting of: a cone, a pyramid, a triangular pyramid and a polygonal pyramid. Each possibility represents a separate embodiment of the present invention. According to some embodiments, the diameter of the sharp tip section at its widest part is larger than the diameter of the middle part of the microneedle at its widest part. According to some embodiments, the middle part of the microneedle is the part of the microneedle comprised in between the sharp tip section of the microneedle's skeleton and the base of the microneedle's skeleton. According to some embodiments, the middle part of the microneedle comprises the middle section of the microneedle's skeleton and the augmentation composition. According to some embodiments, the middle part of the microneedle comprises the middle section of the microneedle's skeleton, at least part of the leakage stopper and the augmentation composition. According to some embodiments, the middle section of the skeleton is a longitudinal core extending substantially from the center of the sharp tip section to the center of the base.

According to some embodiments, the skeleton further comprises a leakage stopper situated between the sharp tip section and the middle section. According to some embodiments, the leakage stopper is configured to prevent leakage of the augmentation composition from the skin of the subject following extraction of the microneedle from the skin of the subject. According to some embodiments, the leakage stopper is integrally formed with the sharp tip section. According to some embodiments, the leakage stopper is in a shape selected from the group consisting of: a cone, a pyramid, a triangular pyramid and a polygonal pyramid. Each possibility represents a separate embodiment of the present invention. According to some embodiments, the widest part of the leakage stopper is facing the widest part of the sharp tip section.

According to some embodiments, the skeleton's base has a shape selected from the group consisting of: a cylinder, a rectangular box, a cuboid, a triangular box and a polygonal box. Each possibility represents a separate embodiment of the present invention.

According to some embodiments, the skeleton is attached to the surface of the substrate intended for being placed proximal to the skin of a subject. According to some embodiments, the skeleton is integrally formed with the surface of the substrate intended for being placed proximal to the skin of a subject. According to some embodiments, the skeleton is at least partly inserted into substrate.

According to some embodiments, the augmentation composition comprises at least 30% biocompatible ceramic material. According to some embodiments, the skin augmentation composition comprises hydroxyapatite, magnesium sulfate and polyethylene glycol. According to some embodiments, the applicator is in a form selected from the group consisting of: a strip and a patch. Each possibility represents a separate embodiment of the present invention. According to some embodiments, the applicator is in a form of a strip. A strip is currently a preferred embodiment since it allows more precise placement than other configurations.

According to some embodiments, the array of microneedles is located on at least a portion of the substrate's surface intended for being placed proximal to the skin of a subject. According to some embodiments, at least part of the substrate's surface intended for being placed proximal to the skin of the subject is an adhesive surface.

According to some embodiments, the applicator is configured for self-application. According to some embodiments, the applicator is disposable after a single use. According to some embodiments, at least part of the applicator is substantially transparent. According to some embodiments, the applicator further comprises a marking indicating the location of the array of microneedles on the substrate.

According to some embodiments, the microneedles are configured for delivery of the augmentation composition. According to some embodiments, the length of the microneedles is from 0.05 mm to 1 mm. According to additional embodiments, the length of the microneedles of the invention is up to 2 mm. According to some embodiments, the length of the microneedles is variable in correlation to the location of the microneedles on the substrate.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 4A-C schematically show microneedles, according to some embodiments of the invention.

FIG. 4D shows a cross section along line C-C of the applicator of FIG. 4A, according to some embodiments of the invention.

FIG. 4E shows a cross section along line D-D of the applicator of FIG. 4A, according to some embodiments of the invention.

FIGS. 6A-D schematically show application of an applicator to a deep skin line or deficiency, according to some embodiments of the invention.

FIGS. 8 A-E schematically show a manufacturing procedure for microneedles, according to some embodiments of the invention.

DETAILED DESCRIPTION OF THE INVENTION

Figure 1A:
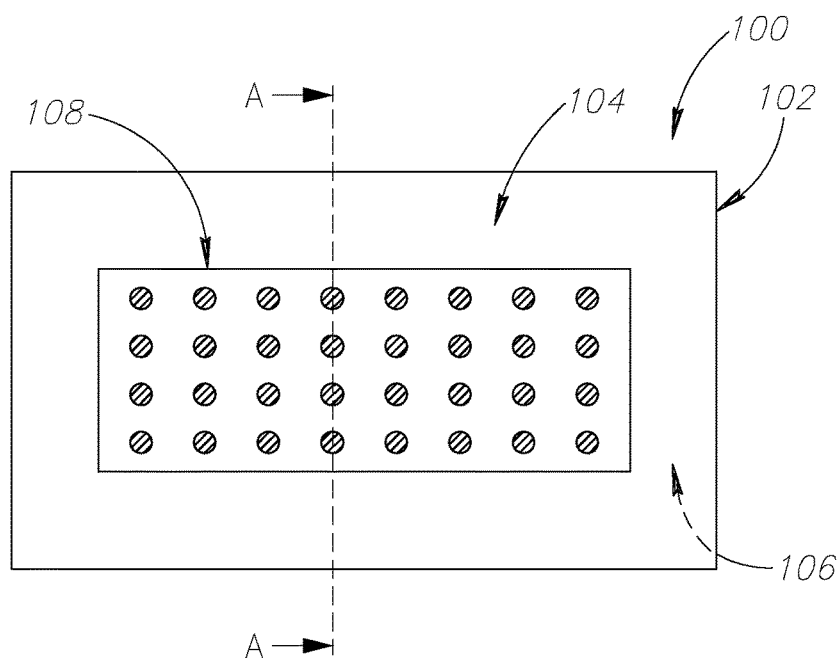
FIG. 1A schematically shows an applicator, according to some embodiments of the invention, in the form of a patch.

The present invention provides, for the first time, a microneedle-based applicator for delivery of a skin augmentation composition to the skin of a subject, the composition comprising at least one biocompatible ceramic material. The applicators of the invention provide an efficient, comfortable and easy-to-use delivery system for skin augmentation compositions. The present invention further provides delivery methods of skin augmentation compositions to the skin of a subject. The methods of the invention enable, inter alia, filling of undesired folds, wrinkles, or lines in a subject's skin. According to some embodiments, the methods of the invention enable a subject to use the applicators and methods of the invention without the help of a trained medical professional. According to other embodiments, the applicators of the invention may be supplied as disposable strips or patches. Each possibility represents a separate embodiment of the present invention.

According to one aspect, the present invention provides an applicator configured for administration of a skin augmentation composition to a skin of a subject, the applicator comprising a substrate, wherein the substrate has a generally flattened structure having two opposing surfaces, wherein one surface is intended for being placed proximal to the skin of a subject and the other surface facing away from the skin of the subject; and an array of microneedles, wherein the array of microneedles is located on the surface proximal to the skin of the subject, the array comprising a multiplicity of microneedles, wherein each of the microneedles comprises:
- a skeleton made of a rigid material, the skeleton comprises:
  - a sharp tip section located on one end of the skeleton, the sharp tip section being
  - configured to penetrate a skin of a subject;
  - a base on an opposing end of the skeleton; and
  - a middle section connecting between the sharp tip section and the base; and
- a skin augmentation composition comprising at least one biocompatible ceramic material, wherein the augmentation composition at least partly surrounds the middle section, such that a diameter of the sharp tip section is larger than a diameter of the augmentation composition.

According to another aspect, the present invention provides a microneedle for administration of a skin augmentation composition to a skin of a subject, the microneedle comprising:
- a skeleton made of a rigid material, the skeleton comprises:
  - a sharp tip section located on one end of the skeleton, the sharp tip section being
  - configured to penetrate a skin of a subject;
  - a base on an opposing end of the skeleton; and
  - a middle section connecting between the sharp tip section and the base; and
- a skin augmentation composition comprising at least one biocompatible ceramic material, wherein the augmentation composition at least partly surrounds the middle section, such that a diameter of the sharp tip section is larger than a diameter of the augmentation composition.

According to some embodiments, the applicator and/or microneedle of the invention are configured for administration of a skin augmentation composition to a skin of a subject or a sub-cutis of a subject or a combination thereof. Each possibility represents a separate embodiment of the present invention.

According to some embodiments, the term "skin augmentation" refers to increasing the volume of the treated skin and/or sub-cutis. According to some embodiments, the term "skin augmentation" refers to increasing the apparent volume of the treated skin.

According to some embodiments, the substrate is in a form selected from the group consisting of: a strip and a patch. Each possibility represents a separate embodiment of the present invention. According to some embodiments, the substrate is in the form of a strip. According to some embodiments, the substrate is in the form of a patch. A strip is currently a preferred embodiment since it allows more precise placement than other configurations.

As used herein, the term "strip" refers to a longitudinal shape having a first end and a second end. According to some embodiments, the substrate comprises a first surface intended for being proximal to the skin and a second surface facing away from the skin. As used herein, the term "proximal" refers to a side which is close to the skin of a subject. As used herein, the term "proximal side" and "proximal part" are interchangeable. According to some embodiments, the terms "the proximal surface", "the surface intended for being placed proximal to the skin of a subject" and "the inner surface" are used interchangeably. As used herein, the terms "patient" and "subject" are used interchangeably.

According to some embodiments, the microneedles are located on at least part of the proximal surface of the substrate. According to some embodiments, at least part of the proximal surface of the substrate comprises an adhesive. According to some embodiments, the microneedles are not co-localized with the adhesive on the proximal surface of the substrate. According to some embodiments, the microneedles are co-localized with the adhesive on the proximal surface of the substrate. According to some embodiments, the microneedles are at least partially co-localized with the adhesive on the proximal surface of the substrate. As used herein, the term "co-localized" refers to being situated at the same two-dimensional coordinates.

According to some embodiments, the substrate is flexible. According to some embodiments, the applicator is adaptable to the outlines of a skin which requires augmentation. According to some embodiments, the substrate is adaptable to the outlines of a skin which requires augmentation. In a non-limiting example, the applicator of the invention may be applied to a subject's face such that it adapts to the outlines and contours of the face. Applying the flexible applicator to a subject's face such that the applicator adapts to the outline of the face may enable efficient delivery of the skin augmentation composition to the desired site. According to some embodiments, the applicator is curved. According to some embodiments, the applicator is curved so as to fit to the contours of a skin which requires augmentation.

According to some embodiments, the applicator comprises a plurality of segments. According to some embodiments, the segments are configured to flexibly move relative to one another. According to some embodiments, each segment comprises an array of microneedles comprising the skin augmentation composition of the invention. According to some embodiments, each segment comprises a substrate and an array of microneedles comprising the skin augmentation composition of the invention. According to other embodiments, the applicator comprises a plurality of segments and a single array of microneedles. According to some embodiments, the segments are attached to one another. According to some embodiments, the segments are integrally formed with one another. An applicator comprising a plurality of segments configured to flexibly move relative to one another may enable precise placement of the applicator over the undesired lines, wrinkles, depressed scars or folds to be treated. According to some embodiments, the size and/or number of the segments varies so as to enable precise placement of the applicator over the lines, wrinkles, depressed scars or folds to be treated. Each possibility represents a separate embodiment of the present invention. According to some embodiments, the applicator comprises segments of different sizes. As used herein, the terms "a plurality of" and "a multiplicity of" are used interchangeably and refer to at least two. As used herein, the terms "made of" and "composed of" are used interchangeably. According to some embodiments, the applicator further comprises a removable shield or cover or sheath configured to protect the microneedles prior to insertion into a subject.

According to some embodiments, the applicator may be of any shape and size. According to some embodiments, the substrate may be of any shape and size. According to other embodiments, the applicator is of a shape and size enabling efficient delivery of a skin augmentation composition to a subject in need thereof. According to some embodiments, the applicator is of a shape and size which fit treatment areas on a subject. Non-limiting examples are strips, which may fit longitudinal lines or wrinkles, and patches which may fit larger skin folds, depressed scars or defects to be treated.

According to other embodiments, different applicators according to the invention may comprise different amounts of skin augmentation composition. According to some embodiments, different microneedles within the same applicator comprise a different amount of skin augmentation composition. According to other embodiments, different applicators of the invention may comprise different numbers of microneedles. According to some embodiments, the microneedles comprised in the applicators of the inventions may be arranged in different conformations. According to some embodiments, the microneedles comprised in the applicators of the invention may be of different sizes. According to some embodiments, the microneedles comprised in the applicator of the invention are arranged as a single array. According to some embodiments, the microneedles comprised in the applicator of the invention are arranged as multiple arrays. According to some embodiments, the microneedles comprised in the applicator of the invention are arranged as multiple arrays, wherein each array is comprised in a different segment of the applicator. According to some embodiments, the spacing between each 2 microneedles in the same microneedles array is between 0.1-2 mm. According to some embodiments, the spacing between each 2 microneedles in the same microneedles array is at least 0.1, 0.2, 0.3, 0.4, 0.5, 0.6, 0.7, 0.8, 0.9, 1, 1.2, 1.4, 1.6, 1.8, 2 mm. Each possibility represents a separate embodiment of the present invention. According to some embodiments, the spacing between each 2 microneedles in the same microneedles array is at least spacing which enables flexibility of the applicator of the invention and/or adaptability of the applicator to the outlines of a skin which requires augmentation. Each possibility represents a separate embodiment of the present invention.

As used herein, the term "biodegradable" refers to a material which is naturally degraded when in a subject's body, by enzymatic activity, chemical dissolution or otherwise. As used herein, the term "biocompatible" refers to a material which does not elicit any undesirable and/or toxic local or systemic effects when administered to a subject.

According to some embodiments, the substrate may be of any material known in the art, as long as it is able to support microneedles and a skin augmentation composition. According to some embodiments, the substrate is made of a non-biodegradable material. According to some embodiments, the substrate is made of a rigid material. Non-limiting examples of materials suitable for making the substrate are: a metal, a polymer, medical plastic, a rubber, latex or a combination thereof. Each possibility represents a separate embodiment of the present invention. Suitable polymers for making the applicator may include, for instance, polyethylene terephthalate, polyvinylchloride, polyethylene, polypropylene, polycarbonate, polyester, and so forth. According to some embodiments, at least part of the substrate is made of a rigid material. According to some embodiments, at least part of the substrate is made of a flexible material.

According to some embodiments, the substrate and the base of the microneedles are made of a non-biodegradable material. As used herein, the base of the microneedle refers to the base of the microneedle's skeleton. According to some embodiments, the skeleton of the microneedles and at least part of the substrate are made of a non-biodegradable material. According to some embodiments the base of the microneedles and at least part of the substrate are made of a unitary piece of a non-biodegradable material. According to some embodiments, the base of the microneedles and at least part of the substrate are integrally formed. According to some embodiments, the skeleton of the microneedles and at least part of the substrate are made of a unitary piece of a non-biodegradable material. According to some embodiments, the skeleton of the microneedles and at least part of the substrate are integrally formed. According to some embodiments, the skeleton of the microneedle is integrally formed with at least part of the surface of the substrate intended for being placed proximal to the skin of a subject. According to some embodiments, the skeleton of the microneedle is attached to the substrate. According to some embodiments, the skeleton of the microneedle is attached to the surface of the substrate intended for being placed proximal to the skin of a subject. According to some embodiments, the skeleton of the microneedle is at least partly inserted into the substrate. According to some embodiments, microneedles having a skeleton at least partly inserted into the substrate of the applicator are more stably secured to the substrate than microneedles that are attaches and/or integrally formed with the substrate. Each possibility represents a separate embodiment of the present invention.

According to some embodiments, the middle section of the microneedle's skeleton passes through a tight-fitting opening in the skeleton's base and is at least partly inserted into the substrate or the substrate surface intended for being placed proximal to the skin of a subject. Each possibility represents a separate embodiment of the present invention. According to some embodiments, the middle section of the microneedle's skeleton passes through a tight-fitting opening in the skeleton's base and is at least partly inserted into the substrate or the substrate surface intended for being placed proximal to the skin of a subject, such that the middle section is perpendicular to the base and the substrate. Each possibility represents a separate embodiment of the present invention.

According to some embodiments, the middle part of the microneedle is the part of the microneedle comprised in between the sharp tip section of the microneedle's skeleton and the base of the microneedle's skeleton, comprising the middle section of the microneedle's skeleton and the augmentation composition. According to some embodiments, only the middle part of the microneedle comprises the skin augmentation composition. According to some embodiments, the sharp tip section of the microneedle's skeleton does not contain the skin augmentation composition. According to some embodiments, the base of the microneedle does not contain the skin augmentation composition.

According to some embodiments, the applicator is configured to be applied by a medical professional. According to some embodiments, the applicator is configured for self-application. It is to be understood that a subject may be able to use the applicator and methods of the invention without the help of a trained medical professional. According to some embodiments, the applicator is disposable after a single use. According to some embodiments, following removal of the applicator from the skin of the subject the applicator is substantially devoid of blood or other biohazardous substances following use of the applicator. As used herein "substantially devoid" is devoid other than trace amounts.

According to some embodiments, at least part of the applicator is substantially transparent. According to some embodiments, at least part of the substrate is substantially transparent. According to some embodiments, only the part of the applicator comprising the microneedles is substantially transparent. According to some embodiments, only the part of the substrate comprising the microneedles is substantially transparent. According to some embodiments, at least the part of the substrate not comprising an adhesive surface is substantially transparent. As used herein, "substantially transparent" refers to a material having an opacity level which enables seeing the skin to be treated through the material. Using an applicator comprising a substrate which is substantially transparent, according to the present invention, may enable seeing the site of skin defect or deficiency through the applicator and thus enable accurate placement of the applicator. According to some embodiments, at least part of the substrate and/or at least part of the microneedles are substantially transparent. Each possibility represents a separate embodiment of the present invention.

According to some embodiments, at least part of each microneedle is substantially transparent. According to some embodiments, at least part of the microneedle's skeleton is substantially transparent. According to some embodiments, the microneedle's skeleton is substantially transparent. According to some embodiments, at least the base of the microneedles is substantially transparent. According to some embodiments, at least the base of the microneedles and a part of the substrate are substantially transparent. According to some embodiments, at least part of the substrate is substantially transparent and the microneedles are not substantially transparent. According to some embodiments, clearly visible microneedles which are not substantially transparent, comprised in a substantially transparent substrate according to the invention, assist in placing the applicator accurately over the site of skin defect or deficiency.

According to some embodiments, the applicator further comprises a marking indicating the location of the array of microneedles on the substrate. According to some embodiments, the marking indicating the location of the array of microneedles on the substrate is on the surface of the substrate facing away from the skin. According to some embodiments, the marking indicating the location of the array of microneedles on the substrate is on the surface proximal to the skin. According to some embodiments, the marking indicating the location of the array of microneedles on the substrate is both on the surface of the substrate facing away from the skin and the surface of the substrate proximal to the skin. According to some embodiments, the marking is in the form of dots or the like, each dot representing the location of a single microneedle in the microneedle array. According to some embodiments, the marking delineates the general location of the entire microneedle array on the substrate. According to some embodiments, the marking indicating the location of the array of microneedles on the substrate assists in accurately placing the applicator over the site of skin defect or deficiency, thus delivering the skin augmentation composition to the exact site of skin defect or deficiency.

Non-limiting examples of a skin defect or deficiency, according to some embodiments of the present invention, are selected from the group consisting of: undesired lines, wrinkles, folds, depressed scars, areas of skin or sub cutis deficiency or a combination thereof. Each possibility represents a separate embodiment of the present invention.

As used herein, the terms "composition", "the composition of the invention" "augmentation composition", "a soft tissue augmentation composition" and "skin augmentation composition" are used interchangeably and refer to a composition comprising at least one biocompatible ceramic skin augmentation material. It is to be understood that a skin augmentation composition according to the present invention is suitable for filling of skin, of sub-cutis or a combination thereof.

As used herein, the terms "biocompatible ceramic skin augmentation material", "biocompatible ceramic soft tissue augmentation material", "biocompatible ceramic agent", "biocompatible ceramic" and "biocompatible ceramic material" are used interchangeably. As used herein, the term "biocompatible ceramic material", refers to a biocompatible skin augmentation material having ceramic properties. According to some embodiments, the biocompatible ceramic material is an inorganic ceramic material, such as, but not limited to, hydroxyapatite. According to some embodiments, the biocompatible ceramic material is water-insoluble. According to some embodiments, the biocompatible ceramic material is a calcium phosphate ceramic material. According to some embodiments, the biocompatible ceramic material is hydroxyapatite. As used herein, the terms "hydroxyapatite", "hydroxylapatite", "calcium hydroxyapatite" and "calcium hydroxylapatite" are interchangeable. According to some embodiments, hydroxyapatite as used herein refers to a salt or derivative of hydroxyapatite.

A non-limiting example of a skin augmentation composition comprising a biocompatible ceramic material is RADIESSE® manufactured by Merz Aesthetics, comprising calcium hydroxylapatite beads suspended in a gel carrier that consists primarily of water, glycerin and sodium carboxymethylcellulose.

According to some embodiments, a biocompatible ceramic material is biodegradable. According to some embodiments, a biocompatible ceramic material is capable of undergoing biodegradation not less than 1, 2, 3, 4 weeks following administration to a subject. Each possibility represents a separate embodiment of the present invention. According to some embodiments, a biocompatible ceramic material is capable of undergoing biodegradation not less than 1, 2, 3, 4, 5, 6, 7, 8, 9, 10, 11, 12 months following administration to a subject. Each possibility represents a separate embodiment of the present invention. According to some embodiments, a biocompatible ceramic material is capable of undergoing biodegradation not less than 0.5, 1, 2, 3 years following administration to a subject. Each possibility represents a separate embodiment of the present invention. Typically, a biocompatible ceramic material is capable of undergoing biodegradation not less than 12 months following administration to a subject.

According to some embodiments, the biodegradation of a biocompatible ceramic material is significantly slower than biodegradation of skin augmentation materials selected from the group consisting of: bovine collagen, porcine collagen, recombinant collagen, human collagen, hyaluronic acid and hyaluronic acid derivatives, gelatin matrices and combinations thereof. Each possibility represents a separate embodiment of the present invention.

According to some embodiments, the biocompatible ceramic material is in the form of beads and/or particles. Each possibility represents a separate embodiment of the present invention. According to some embodiments, the biocompatible ceramic material comprises beads and/or particles having the same/different sizes. Each possibility represents a separate embodiment of the present invention. According to some embodiments, the biocompatible ceramic material is in the form of beads and/or particles of a size suitable for the size of the treated area. Each possibility represents a separate embodiment of the present invention. According to some embodiments, applicators which contain large beads of a biocompatible ceramic material are suitable for treating deep and/or large lines, wrinkles or folds.

According to some embodiments, the biocompatible ceramic material comprises beads and/or particles having a size of up to 5, 10, 20, 30, 40, 50, 60, 70, 80, 90, 100 μm. Each possibility represents a separate embodiment of the present invention. According to some embodiments, the biocompatible ceramic material comprises beads and/or particles having a size of 25-45 μm. Each possibility represents a separate embodiment of the present invention. According to some embodiments, the biocompatible ceramic material comprises beads and/or particles having a size of 10-50 μm. Each possibility represents a separate embodiment of the present invention. According to some embodiments, the biocompatible ceramic material comprises beads and/or particles having a size of 5-20 μm. Each possibility represents a separate embodiment of the present invention. According to certain embodiments, the biocompatible ceramic material comprises beads and/or particles having a size of about 40 μm. Each possibility represents a separate embodiment of the present invention. According to some embodiments, the biocompatible ceramic material particles are of about 10-100 micrometers, preferably of about 40 micrometers. Each possibility represents a separate embodiment of the present invention.

According to some embodiments, the skin augmentation composition comprises at least 1, 2, 3, 4, 5, 10, 15, 25, 30, 40, 50, 60, 70, 80, 90, 95 percent biocompatible ceramic material. Each possibility represents a separate embodiment of the present invention. According to some embodiments, the skin augmentation composition comprises at least 30% biocompatible ceramic material.

According to some embodiments, the composition of the invention comprises at least one biodegradable carrier. According to some embodiments, the composition of the invention comprises at least one biocompatible ceramic and at least one biodegradable carrier. According to some embodiments, the composition of the invention comprises at least one biocompatible ceramic, at least one biodegradable carrier and at least one additional skin augmentation material. According to some embodiments, the composition of the invention comprises hydroxyapatite and at least one biodegradable carrier. According to some embodiments, the composition of the invention comprises hydroxyapatite and polyethylene glycol. According to some embodiments, the composition of the invention comprises hydroxyapatite, polyethylene glycol and magnesium sulfate.

According to some embodiments, the biodegradable carrier is selected from the group consisting of: a salt, a biodegradable polymer and a combination thereof. Each possibility represents a separate embodiment of the present invention. According to some embodiments, the biodegradable carrier is a salt. According to some embodiments, the salt is a water-soluble salt. According to some embodiments, the salt is selected from the group consisting of: sodium sulfate, sodium chloride, magnesium sulfate, magnesium citrate, magnesium chloride and a combination thereof. Each possibility represents a separate embodiment of the present invention.

According to some embodiments, the biodegradable carrier is a biodegradable polymer. According to some embodiments, the biodegradable polymer is a polymer selected from the group consisting of: Polyethylene glycol (PEG), Polyglactin 910, Polyglecaprone 25, Polydioxanone, Lactomer 9-1, Glycomer 631, Polyglyconate and combinations thereof. Each possibility represents a separate embodiment of the present invention. According to some embodiments, the biodegradable carrier is magnesium sulfate and/or polyethylene glycol. Each possibility represents a separate embodiment of the present invention. According to some embodiments, PEG as used herein has a molecular weight between 20 and 50 kDa. According to some embodiments, a biodegradable carrier comprising PEG of 20-50 kDa has a thick paste consistency. According to some embodiments, the biodegradable carrier is Polyglactin 910 and/or magnesium sulfate. Each possibility represents a separate embodiment of the present invention.

According to some embodiments, the biodegradable carrier is degradable within 1, 2, 3, 4, 5, 6, 7, 8, 9, 10, 12 hours of inserting the microneedles into the skin of a subject. Each possibility represents a separate embodiment of the present invention. According to some embodiments, the biodegradable polymer is degradable within 1, 2, 3, 4, 5, 6, 7, 8, 9, 10, 12 hours of inserting the microneedles into the skin of a subject. Each possibility represents a separate embodiment of the present invention. According to some embodiments, the biodegradable carrier is degradable within 0.5, 1, 2, 3, 4, 5, 6, 7 days of inserting the microneedles into the skin of a subject. Each possibility represents a separate embodiment of the present invention. According to some embodiments, the biodegradable polymer is degradable within 0.5, 1, 2, 3, 4, 5, 6, 7 days of inserting the microneedles into the skin of a subject. Each possibility represents a separate embodiment of the present invention. Typically, the biodegradable carrier undergoes biodegradation within less than 7 days of inserting the microneedles into the skin of a subject, preferably less than 2 days, most preferably less than 1 day. Each possibility represents a separate embodiment of the present invention. Without wishing to be bound by any theory or mechanism, rapid biodegradation of the biodegradable carrier within hours/days of introduction into the body of a subject results in uniform distribution of the biocompatible ceramic material and/or the skin augmentation material in the treated area, thus achieving uniform filing of the treated skin defect/deficiency. According to some embodiments, following insertion of the composition of the invention to the skin of the subject, the biodegradable carrier undergoes biodegradation and the biocompatible ceramic remains within the skin of a subject for at least several months, preferably up to a year, most preferably more than a year. Each possibility represents a separate embodiment of the present invention.

According to some embodiments, insertion of microneedles comprising the skin augmentation composition to the skin of a subject results in biodegradation of fast-degrading elements in the composition, thus resulting in release of the biocompatible ceramic into the treated area. According to some embodiments, the fast-degrading element is a biodegradable carrier such as, but not limited to, magnesium sulfate and/or polyethylene glycol. Each possibility represents a separate embodiment of the present invention. It is to be understood that, according to some embodiments, biodegradation of elements in the composition such as a biodegradable carrier assist in homogenous spreading of the biocompatible ceramic in the treated area. According to some embodiments, following biodegradation of fast-degrading elements, such as a biodegradable carrier, the biocompatible ceramic is transferred from the microneedle to the treated area. As used herein, fast-degrading elements refer to elements within the composition of the invention which undergo biodegradation within hours or up to 7 days from insertion of the microneedles of the invention into the skin of a subject. It is to be understood that a biocompatible ceramic is not a fast-degrading element of the composition of the invention. According to some embodiments, following administration of the applicator of the invention for a desired period of time, the applicator and the microneedles are removed from the subject, while at least part of the composition remains in the treated area.

According to some embodiments, the biodegradable carrier comprises water and/or glycerol and/or carboxymethylcellulose. Each possibility represents a separate embodiment of the present invention. According to some embodiments, the biodegradable carrier comprises water, glycerol and carboxymethylcellulose. According to some embodiments, the biodegradable carrier comprises carboxymethylcellulose.

According to some embodiments, the composition of the invention comprises a biocompatible ceramic material in the form of beads and/or particles. Each possibility represents a separate embodiment of the present invention. According to some embodiments, the composition of the invention comprises a biocompatible ceramic material in the form of beads and/or particles surrounded by at least one biodegradable carrier. Each possibility represents a separate embodiment of the present invention. According to some embodiments, the composition of the invention comprises a biocompatible ceramic material in the form of beads and/or particles surrounded by at least one biodegradable polymer. Each possibility represents a separate embodiment of the present invention. According to some embodiments, the composition of the invention comprises a biocompatible ceramic material in the form of beads and/or particles surrounded by at least one salt. Each possibility represents a separate embodiment of the present invention. According to some embodiments, the composition of the invention comprises hydroxyapatite in the form of beads and/or particles. Each possibility represents a separate embodiment of the present invention. According to some embodiments, the composition of the invention comprises hydroxyapatite in the form of beads and/or particles surrounded by at least one biodegradable carrier. Each possibility represents a separate embodiment of the present invention.

Without wishing to be bound by any theory or mechanism, beads or particles of a biocompatible ceramic material such as, but not limited to, hydroxyapatite, surrounded by a biodegradable carrier, may homogeneously spread in the treated area upon degradation of the biodegradable carrier by dissolution, enzymatic activity and the like.

According to some embodiments, adding a biodegradable polymer to the composition of the invention results in a composition having a gel, a paste or a solid like consistency. Each possibility represents a separate embodiment of the present invention. According to some embodiments, a gel, a paste or a solid like composition may be easily inserted into the middle part of the microneedles of the invention. According to some embodiments, addition of a salt to the composition of the invention assists in uniform dispersion of the biocompatible ceramic within the composition. Without wishing to be bound by any theory or mechanism, addition of a salt to the composition of the invention may result in water diffusion into the composition, thus assisting in uniform dispersion of the biocompatible ceramic within the composition and/or within the treated area.

As used herein, the terms "skin augmentation material" and "filler" refer to agents and compositions useful for augmentation of skin defects. According to some embodiments, a skin augmentation material is a dermal and/or sub-dermal filler. Each possibility represents a separate embodiment of the present invention. Suitable skin augmentation materials according to the invention include, but are not limited to, proteins, polysaccharides, lipids, synthetic polymers and combinations thereof. Each possibility represents a separate embodiment of the present invention. According to some embodiments, a skin augmentation material according to the invention is any material known in the art which is suitable for filling undesired fold, wrinkle, depressed scar or line in a skin of a subject. According to some embodiments, a skin augmentation material according to the invention is any skin augmentation material which may be delivered using microneedles. According to some embodiments, a biocompatible ceramic material is a skin augmentation material. According to certain embodiments, a skin augmentation material refers to a biocompatible, inert material. "Inert material" as used herein refers to a non-antigenic, non-carcinogenic, non-teratogenic, and non-migratory augmentation material.

According to some embodiments, skin augmentation materials include allogeneic products, xenogeneic products and synthetically derived products. Each possibility represents a separate embodiment of the present invention.

According to some embodiments, the skin augmentation composition comprises at least one biocompatible ceramic material and at least one additional type of skin augmentation material. According to some embodiments, the composition of the invention further comprises at least one skin augmentation material selected from the group consisting of: a biodegradable natural substance, a biodegradable synthetic polymer, a non-biodegradable synthetic polymer and combinations thereof. Each possibility represents a separate embodiment of the present invention. According to some embodiments, the composition of the invention further comprises at least one skin augmentation material selected from the group consisting of: a biodegradable natural substance, a biodegradable synthetic polymer, a non-biodegradable synthetic polymer, a non-biodegradable natural substance and combinations thereof. Each possibility represents a separate embodiment of the present invention.

According to some embodiments, a biodegradable natural substance is selected for example from the group consisting of: bovine collagen, porcine collagen, recombinant collagen, human collagen, gelatin, hyaluronic acid, hyaluronic acid derivative, dried acellular particulate dermal matrix, allogeneic fat and combinations thereof. Each possibility represents a separate embodiment of the present invention.

According to some embodiments, a biodegradable synthetic polymer is selected for example from the group consisting of: poly-L-lactic acid, polyethylene oxide, carboxymethylcellulose and combinations thereof. Each possibility represents a separate embodiment of the present invention.

According to some embodiments, a non-biodegradable synthetic polymers is selected for example from the group consisting of: polymethyl methacrylate (PMMA), polymethyl methacrylate beads, silicones, silicone rubber, expanded polytetrafluoroethylene (ePTFE), polyacrylamide, polyalkylimide and combinations thereof. Each possibility represents a separate embodiment of the present invention.

According to some embodiments, the skin augmentation composition of the invention comprises a combination of materials comprising at least one biocompatible ceramic material and at least one additional type of skin augmentation material. According to some embodiments, the skin augmentation composition of the invention comprises a combination of materials comprising at least one biocompatible ceramic material and at least one type of skin augmentation material other than a biocompatible ceramic material. According to some embodiments, the skin augmentation composition comprises at least one biocompatible ceramic material, a biodegradable carrier and at least one type of skin augmentation material selected from the group consisting of: a biodegradable natural substance, a biodegradable synthetic polymer, a non-biodegradable synthetic polymer and combinations thereof. Each possibility represents a separate embodiment of the present invention.

According to some embodiments, the skin augmentation composition comprises hydroxyapatite. According to some embodiments, the skin augmentation composition comprises hydroxyapatite and at least one type of skin augmentation material other than hydroxyapatite. According to some embodiments, the skin augmentation composition comprises hydroxyapatite and at least one type of soft-tissue augmentation material selected from the group consisting of: a biodegradable natural substance, a biodegradable synthetic polymer, a non-biodegradable synthetic polymer, a non-biodegradable natural substance and combinations thereof. Each possibility represents a separate embodiment of the present invention. According to some embodiments, the skin augmentation composition comprises hydroxyapatite and at least one type of soft-tissue augmentation material selected from the group consisting of: a biodegradable natural substance, a biodegradable synthetic polymer, a non-biodegradable synthetic polymer and combinations thereof. Each possibility represents a separate embodiment of the present invention.

According to some embodiments, the composition of the invention comprises less than 50% weight percent water-soluble skin augmentation materials such as, but not limited to, collagen, hyaluronic acid and gelatine. Each possibility represents a separate embodiment of the present invention.

Preferably, skin augmentation materials which may be comprised in the composition of the invention are effective dermal fillers approved by the U.S. Food and Drug administration, including but not limited to fillers comprising structural proteins, polysaccharides or synthetic polymers. Exemplary embodiments of skin augmentation materials that may be used include collagen, such as reconstituted bovine collagen products including, but not limited to, ZYDERM I®, ZYDERM II® and ZYPLAST® (Collagen Corporation); natural human collagen COSMODERM™ and COSMOPLAST™ (NAMED); and endogenous collagen from the subject, AUTOLOGEN® produced by Collagenesis. Additional examples of dermal fillers may be selected from those comprising hyaluronic acid, including but not limited to, such products as HYLAFORM® gel manufactured by NAMED and Genzyme Corporations, derived from the rooster combs of domestic fowl; and RESTYLANE® manufactured by Medicis, a hyaluronic acid derivative derived from streptococcal bacterial fermentation. Hyaluronic acid according to the present invention includes both non-cross-liked and/or cross-linked hyaluronic acid derivatives as are well known in the art. Each possibility represents a separate embodiment of the present invention. According to some embodiments, collagen according to the invention is selected from the group consisting of: allogeneic collagen, xenogeneic collagen and a combination thereof. Each possibility represents a separate embodiment of the present invention. According to other embodiments, a skin augmentation material is human cadaveric dermis cultivated from a cadaver, such as, but not limited to, the materials having the brand names Cymetra, Dermalogen, Alloderm and Fascian.

According to some embodiments, the applicator of the invention comprises a biologically active agent. According to some embodiments, the composition of the invention comprises a biologically active agent. According to some embodiments, the biologically active agent is selected from the group consisting of: an enzyme, a drug, a toxin and a combination thereof. Each possibility represents a separate embodiment of the present invention.

According to some embodiments, the drug is an analgesic. According to some embodiments, when the applicator of the invention is used to deliver skin augmentation composition subcutaneously, at least one analgesic is co-delivered by the applicator of the invention together with the skin augmentation composition. According to some embodiments, the skin augmentation composition of the invention further comprises an analgesic. According to some embodiments, the methods of the invention further comprise administration of an analgesic. According to some embodiments, every analgesic known in the art may be used with the present invention, such as, but not limited to: lidocaine, paracetamol, non-steroidal anti-inflammatory drug (NSAID), COX-2 inhibitor, opiates or morphinomimetics. Each possibility represents a separate embodiment of the present invention. According to some embodiments, an analgesic which may be used with the present invention is lidocaine.

According to some embodiments, the drug is a drug known in the art to assist in filling undesired lines, wrinkles, folds and the like. According to some embodiments, examples of drugs which may be comprised in the composition of the invention include, but are not limited to, anti-psoriasis drugs, muscle relaxants and a combination thereof. Each possibility represents a separate embodiment of the present invention.

According to some embodiments, the drug is a drug for treatment of pathological scarring. According to some embodiments, the drug for treatment of pathological scarring is a corticosteroid. According to some embodiments, the corticosteroid is any corticosteroid known in the art for treatment of pathological scarring, such as, but not limited to triamcinolone.

According to some embodiments, the toxin is botulinum toxin. According to some embodiments, the composition of the invention comprises botulinum toxin. According to some embodiments, the applicator of the invention comprises botulinum toxin.

According to some embodiments, the skin augmentation composition of the invention further comprises a medical pigment. According to some embodiments, the microneedles of the invention comprise a medical pigment. As used herein, the term "medical pigment" refers to a color material suitable for insertion into the skin of a subject. According to some embodiments, medical pigments have a regulatory approval for insertion into a skin of a subject. According to some embodiments, medical pigments are pigments known in the art to be suitable for micro-pigmentation treatments. In non-limiting examples, medical pigments suitable for use according to the present invention include, but are not limited to, pigments such as BIOCHROMADERM® (Biotic Phocea) or the Signature Series (Micro-Pigmentation Centre, Inc.). Possible medical pigments for use with the applicator of the present invention may be pigments for scar camouflage, areola reconstruction or lip remodeling.

According to some embodiments, a microneedle comprising a medical pigment is suitable for micro-pigmentation treatments. According to some embodiment, micro-pigmentation treatments are selected from the group consisting of: concealment of scars, concealment and/or blurring of skin pigmentation, nipple areola construction and/or augmentation, correction of freckles, lip coloring, eyebrow coloring and a combination thereof. Each possibility represents a separate embodiment of the present invention. According to some embodiments, the microneedles of the invention comprise a composition comprising a medical pigment. According to some embodiments, the applicator of the invention comprises microneedles comprising a medical pigment without a biocompatible ceramic or a skin augmentation composition. Each possibility represents a separate embodiment of the present invention.

According to some embodiments, the present invention provides an applicator configured for administration of a medical pigment to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises a composition comprising at least one medical pigment. According to some embodiments, the applicator is configured for administration of a medical pigment to a skin of a subject and/or to sub-cutis layers of a subject. Each possibility represents a separate embodiment of the present invention.

According to some embodiments, the microneedles comprise a skeleton made of a rigid material, the skeleton comprising: a sharp tip section located on one end of the skeleton configured to penetrate a skin of a subject, a base on an opposing end of the skeleton and a middle section connecting the sharp tip section and the base; and a composition comprising a medical pigment, wherein the composition at least partly surrounds the middle section, such that a diameter of the sharp tip section is larger than a diameter of the composition.

According to some embodiments, the present invention provides a method for performing a micro-pigmentation treatment on a subject, the method comprises administering to the subject an applicator configured for administration of a medical pigment to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises a composition comprising at least one medical pigment.

According to some embodiments, the applicator of the invention comprises microneedles. According to other embodiments, the applicator of the invention comprises an array of microneedles. According to other embodiments, the applicator of the invention comprises at least one array of microneedles. An array of microneedles may include a mixture of microneedles having, for example, various lengths, diameters, cross-sectional shapes, and spacing between the microneedles. Each possibility represents a separate embodiment of the present invention. According to some embodiments, the length of the microneedles of the invention is typically between about 0.05 and 1 mm, preferably between 10 microns and 500 microns, and more preferably between 30 and 200 microns. Each possibility represents a separate embodiment of the present invention. The length of the microneedles may be selected according to the particular application or treated tissue. Each possibility represents a separate embodiment of the present invention. For certain applications it may be desirable to use microneedles of slightly greater dimensions. Thus, according to some embodiments, the length of the microneedles of the invention is above 1 mm. According to additional embodiments, the length of the microneedles of the invention is up to 2 mm.

According to some embodiments, microneedles longer than 1 mm may be used to deliver the skin augmentation composition subcutaneously. According to some embodiments, microneedles may be used to deliver the skin augmentation composition to areas having deep wrinkles and/or skin deficiency. Each possibility represents a separate embodiment of the present invention. According to some embodiments, microneedles longer than 1 mm may be used to deliver the skin augmentation composition to areas having deep wrinkles and/or skin or sub cutis deficiency. Each possibility represents a separate embodiment of the present invention.

According to some embodiments, the applicator of the invention comprises microneedles having various lengths. According to some embodiments, the applicator of the invention comprises microneedles having variable lengths and/or variable degrees of thickness. Each possibility represents a separate embodiment of the present invention. According to some embodiments, the applicator of the invention comprises microneedles having variable lengths and/or variable degrees of thickness in correlation to the location of the microneedles on the substrate. Each possibility represents a separate embodiment of the present invention. According to some embodiments, the applicator of the invention comprises microneedles having variable lengths in correlation to the location in which they are configured to be situated within the area to be treated. Each possibility represents a separate embodiment of the present invention.

According to some embodiments, microneedles configured to be situated at a deeper point of a line, wrinkle or fold to be treated are longer than microneedles configured to be situated at a superficial point of the line, wrinkle or fold to be treated. In a non-limiting example, microneedles configured to be situated closer to the margins of a line, wrinkle or fold to be treated are shorter than microneedles configured to be situated in the center of the line, wrinkle or fold to be treated. According to some embodiments, microneedles situated at the center of the microneedle array are longer than microneedles situated near the margins of the microneedle array. An applicator comprising microneedles having variable lengths may be able to more precisely and uniformly fill a line, wrinkle or fold.

According to some embodiments, the applicator of the invention comprises microneedles having variable degrees of thickness in correlation to the location in which they are configured to be situated within the area to be treated. According to some embodiments, microneedles configured to be situated at a deeper point of a line, wrinkle or fold to be treated are thicker than microneedles configured to be situated at a superficial point of the line, wrinkle or fold to be treated.

FIG. 1A schematically illustrates a top view of applicator (100) according to some exemplary embodiments. According to the embodiments shown in FIG. 1, applicator (100) includes a substrate (102) shown herein in the form of a rectangular patch, but may have any other form, such as but not limited to, a square, a circle, a strip or any other form. Substrate (102) is preferably made of a flexible material, such as, but not limited to, medical plastic, rubber or latex and is preferably configured to adapt to the curvature of the skin surface. Substrate (102) includes two surfaces: an inner surface (104) and an outer surface (106) Inner surface (104) is configured to be placed proximal to the skin (for example to adhere to the skin) Inner surface (104) includes microneedles array (108).

Figure 2A:
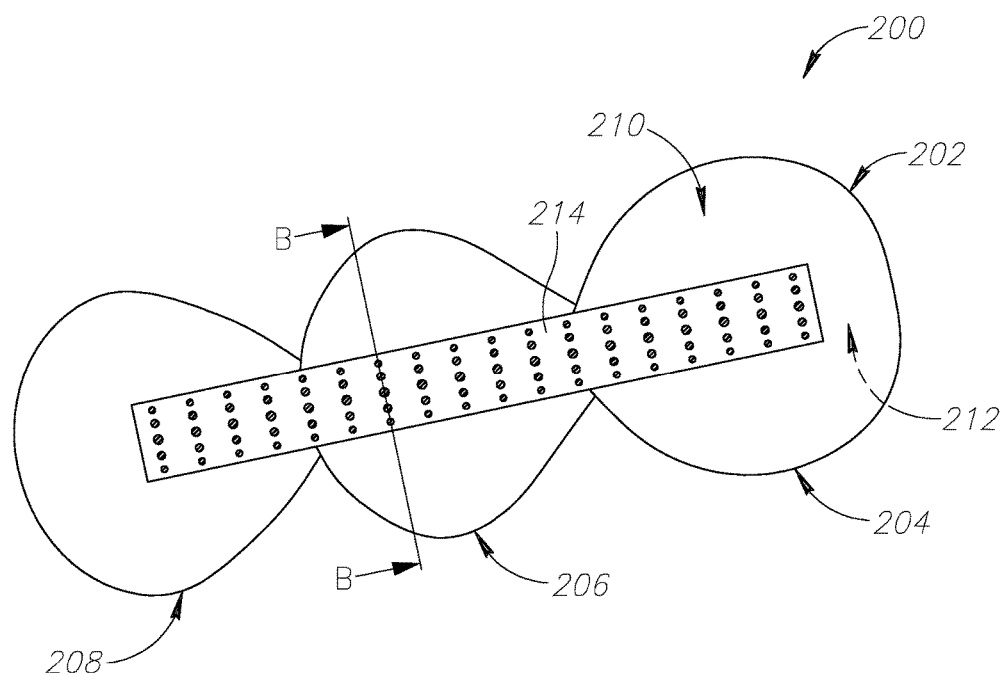
FIG. 2A schematically shows an applicator, according to some embodiments of the invention, in the form of a strip having several segments.

FIG. 2A schematically illustrates a top view of applicator (200) according to some exemplary embodiments. According to the embodiments shown in FIG. 2A, applicator (200) includes substrate (202) in the form of a strip composed of several segments (204, 206, and 208), but can have any other form, such as but not limited to, a rectangle, a square, a circle or any other form. Substrate (202) is preferably made of a flexible material, such as, but not limited to, medical plastic, rubber or latex and is preferably configured to adapt to the curvature of the skin surface. Segments (204, 206, and 208) are preferably configured to flexibly move relative to each other. Substrate (202) includes two surfaces: inner surface (210) and outer surface (212) Inner surface (210) is configured to be placed proximal to the skin (for example to adhere to the skin) Inner surface (210) includes microneedles array (214).

Figure 3:
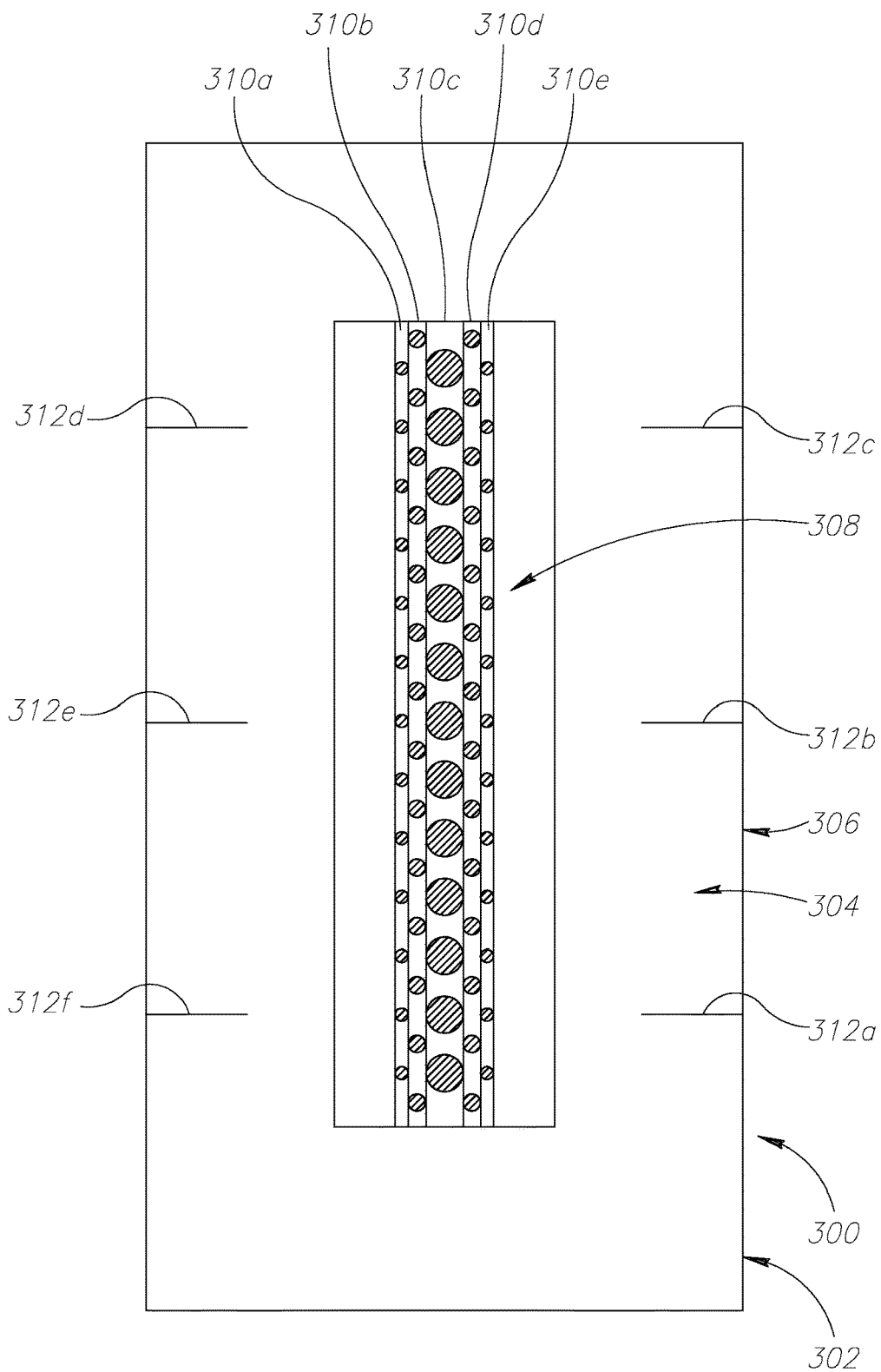
FIG. 3 schematically shows an applicator, according to some embodiments of the invention, in the form of a patch comprising microneedles of various degrees of thickness and having markings indicating the location of the microneedles on the applicator.

FIG. 3 schematically illustrates a top view of applicator (300) according to some exemplary embodiments, showing surface (304) of substrate (302). Surface (304) is intended for being placed proximal to the skin of a subject, while surface (306) is intended to face away from the subject. Surface (304) comprises microneedle array (308). Microneedle array (308) comprises five microneedle rows (310a, 310b, 310c, 310d, 310e), the microneedles being attached to or integrally formed with surface (304). Each possibility represents a separate embodiment of the present invention. Microneedles in microneedle row (310c), situated at the center of array (308) are thicker than microneedles (310b and 310d) which are in turn thicker than microneedles (310a and 310e), situated closer to the ends/margins of array (308). According to some embodiments, thick microneedles are configured to deliver a larger amount of skin augmentation composition than thin microneedles. According to some embodiments, thick microneedles are configured to deliver a large amount of skin augmentation composition to the center/deep region of a wrinkle, line or the like to be treated, requiring higher augmentation than the ends and/or margins of a wrinkle, line or the like. According to other embodiments, thin microneedles are configured to deliver a low amount of skin augmentation composition to the ends and/or margins of a wrinkle, line or the like.

According to the embodiment depicted in FIG. 3, other than the part comprising microneedle array (308), substrate (302) is substantially transparent. Substrate (302) comprises markings (312a, 312b, 312c, 312d, 312e, 312f) indicating the location of microneedle array (308) on surface (304). According to some embodiments, markings (312a, 312b, 312c, 312d, 312e, 312f) assist in correct placement of applicator (300) on the skin of a subject. According to some embodiments, markings (312a, 312b, 312c, 312d, 312e, 312f) are on surface (304) and/or on surface (306). Each possibility represents a separate embodiment of the present invention.

As used herein, the term "microneedles" refers to protruding structures designed to pierce the skin and facilitate delivery of various types of compounds. According to some embodiments, microneedles facilitate delivery of the composition of the invention to dermal and/or sub-dermal compartments of the skin. Each possibility represents a separate embodiment of the present invention. According to some embodiments, subcutaneous delivery of a skin augmentation composition can be achieved by the applicator of the invention if the microneedles comprised in the applicator are longer than the thickness of the skin to be treated. According to some embodiments, the length of the microneedles comprised in the applicator of the invention is configured to allow dermal and/or subcutaneous delivery of a skin augmentation composition. Each possibility represents a separate embodiment of the present invention.

According to some embodiments, the length of the microneedles comprised in the applicator of the invention is configured to allow delivery of skin augmentation composition to the dermis and/or lower layers of the skin. Each possibility represents a separate embodiment of the present invention. According to some embodiments, the microneedles comprised in the applicator of the invention are configured to allow delivery of a skin augmentation composition to the dermis and/or lower layers of the skin without delivery of skin augmentation composition to the epidermis layer of the skin. Each possibility represents a separate embodiment of the present invention. According to some embodiments, the length of the microneedles comprised in the applicator of the invention is configured not to allow delivery of skin augmentation composition to the epidermis. According to some embodiments, the length of the microneedle base is configured not to allow delivery of a skin augmentation composition to the epidermis layer of the skin. According to some embodiments, long microneedles enable delivery of skin augmentation composition to subcutaneously and/or to deep layers of the skin, such as, but not limited to, the hypodermis. Each possibility represents a separate embodiment of the present invention.

According to some embodiments, each microneedle according to the invention comprises the skin augmentation composition and a skeleton made of a rigid material. According to some embodiments, the rigid material is selected from a group consisting of: metal, plastic, a ceramic material, silicone and a combination thereof. Each possibility represents a separate embodiment of the present invention. According to some embodiments, the rigid material is biocompatible. According to some embodiments, the rigid material is biodegradable. According to some embodiments, the rigid material is rigid as to enable the microneedles to be propelled into the skin of the subject. According to some embodiments the rigid material is a metal. According to some embodiments, each microneedle according to the invention comprises the skin augmentation composition and a metal skeleton. According to some embodiments, the metal is selected from the group consisting of: stainless steel, titanium, iron, gold, silver, platinum and a combination and/or alloy thereof. Each possibility represents a separate embodiment of the present invention. According to some embodiments, rigid material is preferably a material approved by the US Food and Drug Association (FDA) for implantation and/or parenteral delivery. Each possibility represents a separate embodiment of the present invention.

According to some embodiments, the skeleton of the microneedles is removed from the subject upon removal of the applicator from the subject. According to some embodiments, upon removal of the applicator of the invention from the skin of the subject the skeletons of the microneedles are removed while at least part of the composition of the invention remains within the skin or subcutaneous region of the subject's skin. Each possibility represents a separate embodiment of the present invention. According to some embodiments, upon removal of the applicator of the invention from the skin of the subject at least part of the biocompatible ceramic remains within the skin or subcutaneous region of the subject's skin, while the microneedles' skeletons are removed. Each possibility represents a separate embodiment of the present invention.

According to some embodiments, the skeleton of each microneedle comprises a sharp tip section, a base and a middle section connecting the sharp tip section and the base. As used herein, the terms "sharp tip section", "tip section" and "tip" are used interchangeably. According to some embodiments, the tip section, the base and the middle section of the skeleton are integrally formed. According to some embodiments, the tip section, the base and the middle section of the skeleton are made of a unitary piece of material. According to some embodiments, the tip section, the base and the middle section of the skeleton are attached to each other.

According to some embodiments, the sharp tip section of the microneedle's skeleton is the most proximal part of the microneedle. As used herein, the proximal side of the microneedle refers to the microneedle's side which is closest to the subject and farthest from the substrate of the applicator. The base part and the sharp tip section of the microneedle's skeleton are on opposing ends of the microneedle's skeleton. As used herein, the base of the microneedle refers to the side of the microneedle which is farthest from the subject and closest to the substrate's surface intended for being placed proximal to the skin of a subject. According to some embodiments, the base of the microneedle's skeleton is the base of the microneedle.

According to some embodiments, the sharp tip section of the microneedle's skeleton is configured to penetrate the skin of a subject. According to some embodiments, the sharp tip section is of any shape which enables it to penetrate the skin of a subject. According to some embodiments, the sharp tip section has a shape selected from the group consisting of: a cone, a pyramid, a triangular pyramid and a polygonal pyramid. Each possibility represents a separate embodiment of the present invention. According to some embodiments, the sharp tip section is attached to the middle section of the microneedle's skeleton. According to some embodiments, the sharp tip section is integrally formed with the middle section of the microneedle's skeleton.

According to some embodiments, the diameter of the sharp tip section is larger than the diameter of the skin augmentation composition. According to some embodiments, the diameter of the sharp tip section is larger than the diameter of the microneedle's middle part. According to some embodiments, the largest diameter of the sharp tip section is larger than the largest diameter of the skin augmentation composition. According to some embodiments, the largest diameter of the sharp tip section is larger than the largest diameter of the microneedle's middle part. As used herein, the diameter of the sharp tip section refers to the largest distance that can be formed between two opposite parallel lines tangent to the boundary of a cross section through the sharp tip section, wherein the cross-section is parallel to the substrate. According to some embodiments, the middle part of the microneedle comprises the middle section of the microneedle's skeleton and the augmentation composition. According to some embodiments, the middle part of the microneedle comprises the middle section of the microneedle's skeleton and the augmentation composition.

According to some embodiments, the sharp tip section punctures the skin of the subject enabling the insertion of the skin augmentation composition. According to some embodiments, a sharp tip section having a larger diameter than the diameter of the skin augmentation composition enables the formation of a skin puncture large enough for the skin augmentation composition to enter into the skin without spillage of the composition outside the body or within the epidermis. Each possibility represents a separate embodiment of the present invention.

According to some embodiments, the base of the microneedles does not comprise the skin augmentation composition. According to some embodiments, the skeleton's base has a shape selected from the group consisting of: a cylinder, a rectangular box, a cuboid, a triangular box and a polygonal box. Each possibility represents a separate embodiment of the present invention. According to some embodiments, the skeleton's base is configured to confer stability to the microneedle. According to some embodiments, the base of the microneedle is configured to prevent the skin augmentation composition from being delivered to the epidermis.

According to some embodiments, the microneedle's base is attached to the substrate. According to some embodiments, the microneedle's base is attached to the substrate's surface intended for being placed proximal to the skin of a subject. According to some embodiments, the microneedle's base is integrally formed with the substrate. According to some embodiments, the microneedle's base is integrally formed with the substrate's surface intended for being placed proximal to the skin of a subject. According to some embodiments, the microneedle's base and the substrate are made of a unitary piece of material. According to some embodiments, the microneedle's base and the substrate's surface intended for being placed proximal to the skin of a subject are made of a unitary piece of material.

According to some embodiments, the length of the base is equal or higher than the thickness of the epidermis at a treated area. Each possibility represents a separate embodiment of the present invention. According to some embodiments, a base having a length equal or higher than the thickness of the epidermis at the treated area prevents delivery of the skin augmentation composition to the epidermis. Preventing delivery of a skin augmentation composition to the epidermis may prevent wasting material, enhance the augmentation effect of the composition or prevent inflammation and/or infection of the treated site. Each possibility represents a separate embodiment of the present invention.

According to certain embodiments, the length of the base is equal or higher than the combined thickness of the epidermis and dermis of the treated area. According to some embodiments, microneedles having a base at least as long as the combined thickness of the epidermis and dermis of the treated area are configured to prevent delivery of the skin augmentation composition to the dermis and the epidermis. According to some embodiments, microneedles having a base at least as long as the combined thickness of the epidermis and dermis of the treated area are configured to deliver the skin augmentation composition subcutaneously. Without wishing to be bound by mechanism, varying the length of the base may determine the skin and/or subcutaneous layer into which the composition is delivered.

According to some embodiments, all the microneedles on the same applicator have the same base length. According to some embodiments, the applicator of the invention comprises microneedles having variable base lengths. According to some embodiments, the length of the base is variable in correlation to the location in which each microneedle is configured to be situated at within a treated area. According to some embodiments, the applicator of the invention comprises microneedles having variable base lengths in correlation to the location of the microneedles on the substrate. According to some embodiments, the applicator of the invention comprises microneedles having variable base lengths in correlation to the thickness of the epidermis and/or dermis at the location each microneedle is configured to be positioned at. Each possibility represents a separate embodiment of the present invention. According to some embodiments, the applicator of the invention comprises microneedles having variable lengths in correlation to the location in which they are configured to be situated within the area to be treated.

According to some embodiments, microneedles configured to be placed at a treatment area having a thick epidermis have a longer base than microneedles configured to be placed at a treatment area having a thin epidermis. It is to be noted that, according to some embodiments, an applicator configured to be placed on a treated area having an epidermis and/or dermis with varying thickness levels may comprise microneedles having bases of varying lengths corresponding to the varying thickness levels. Each possibility represents a separate embodiment of the present invention.

According to some embodiments, microneedles located at the center of a microneedle array comprise a longer base than microneedles located near the edges of the microneedle array. According to some embodiments, microneedles configured to be situated closer to the margins of a line, wrinkle or fold to be treated are comprise a shorter base than microneedles configured to be situated in the center of the line, wrinkle or fold to be treated. According to some embodiments, a microneedle having a long base is configured to deliver the skin augmentation composition to a deeper skin or subcutaneous layer than a microneedle having a short base. Each possibility represents a separate embodiment of the present invention.

According to some embodiments, a diameter of the base is smaller than a diameter of the sharp tip section. According to some embodiments, the largest diameter of the base is smaller than the largest diameter of the sharp tip section. According to some embodiments, the diameter of the base is equal to the diameter of the skin augmentation composition. According to some embodiments, the diameter of the base is equal to the diameter of the microneedle's middle part. As used herein, the diameter of the base refers to the largest distance that can be formed between two opposite parallel lines tangent to the boundary of a cross section through the base of the microneedle, wherein the cross section is parallel to the substrate.

According to some embodiments, the middle section of the microneedle's skeleton is the part of the skeleton connecting between the sharp tip section and the base of the skeleton. According to some embodiments, the skin augmentation composition at least partly surrounds the middle section of the microneedle's skeleton. According to some embodiments, the middle part of the microneedle is the part of the microneedle comprised in between the sharp tip section of the microneedle's skeleton and the base of the microneedle's skeleton. According to some embodiments, the middle part of the microneedle comprises the middle section of the microneedle's skeleton and the augmentation composition According to some embodiments, the middle section of the microneedle skeleton may be in any form suitable for providing the microneedle with rigidity and providing support for the skin augmentation composition. According to some embodiment, the middle section of the skeleton is in the form of a longitudinal core extending substantially from the center of the sharp tip section to the center of the base. According to some embodiment, the middle section of the skeleton comprises a longitudinal core extending substantially from the center of the sharp tip section to the center of the base. As used herein, the term "longitudinal core" refers to a longitudinal piece of a rigid, non-biodegradable, compatible material extending substantially through the center of the microneedle middle part. According to some embodiments, the longitudinal core may be of any shape, such as, but not limited to, a cone, a cylinder, a pyramid, a rectangular box, a triangular box, a polygonal box and the like. According to some embodiments, the longitudinal core has the same dimensions throughout the length of the microneedle's middle part. According to some embodiments, the skeleton's middle section is integrally formed with the sharp tip section. According to some embodiment, the skeleton's middle section is integrally formed with the leakage stopper. According to some embodiments, the skeleton's middle section extends through the base part and is at least partly inserted into the substrate. According to some embodiments, the skeleton's middle section extends through the base part and is at least partly inserted into the substrate perpendicularly. Without wishing to be bound by any mechanism, a skeleton's middle section in the form of a longitudinal core inserted through the base of the skeleton and into the substrate in the form of a cross confers substantial stability to the microneedle. According to some embodiments, the middle section of the skeleton is integrally formed with the microneedle skeleton's base. As used herein, the term "extension", "skeleton extension", "middle section extension", "middle part extension" and "microneedle extension" are used interchangeably and relate to an extension of the middle part of the microneedle's skeleton through the base of the skeleton and at least partly into the substrate of the applicator.

According to some embodiments, the skin augmentation composition at least partly surrounds the middle part of the microneedle's skeleton. According to some embodiments, the skin augmentation composition at least partly surrounds the longitudinal core. According to some embodiments, the skin augmentation composition surrounds the longitudinal core. According to some embodiments, the skin augmentation composition surrounding the skeleton's middle section may form any shape, such as, but not limited to: a cylinder, a rectangular box, a triangular box, a polygonal box and the like.

As used herein, the diameter of the skin augmentation composition refers to the largest distance that can be formed between two opposite parallel lines tangent to the boundary of a cross section through the middle part of the microneedle, wherein the cross section is parallel to the substrate. According to some embodiments, the diameter of the skin augmentation composition refers to the largest distance that can be formed between two opposite parallel lines tangent to the boundary of a cross section through the skin augmentation composition. According to some embodiments, the diameter of the skin augmentation composition refers to the largest distance that can be formed between two opposite parallel lines tangent to the boundary of a cross section through the skin augmentation composition and middle section of the microneedle's skeleton.

According to some embodiments, the microneedle's skeleton further comprises a leakage stopper. According to some embodiments, the leakage stopper is situated between the sharp tip section and the middle section of the microneedle's skeleton. According to some embodiments, the leakage stopper is integrally formed with the sharp tip section and/or the middle section of the skeleton. Each possibility represents a separate embodiment of the present invention. According to some embodiments, the leakage stopper is integrally formed with the sharp tip section. According to some embodiments, the leakage stopper is attached to the sharp tip section.

According to some embodiments, the leakage stopper is configured to prevent leakage of the skin augmentation composition from the skin of the subject following extraction of the microneedle from the skin of the subject. According to some embodiments, the leakage stopper facilitates sliding of the augmentation composition into the treated tissue upon extraction of the microneedles from the skin of the subject. According to some embodiments, the leakage stopper prevents pushing the augmentation composition out of the skin of the subject upon extraction of the microneedles from the skin of the subject. According to some embodiments, the skin augmentation composition at least partly surrounds the leakage stopper. According to some embodiments, the skin augmentation composition at least partly surrounds the middle section of the composition and at least partly surrounds the leakage stopper.

According to some embodiment, the leakage stopper is in a shape selected from the group consisting of: a cone, a pyramid, a triangular pyramid and a polygonal pyramid. Each possibility represents a separate embodiment of the present invention. According to some embodiments, the leakage stopper is in a shape selected from the group consisting of: a cone, a pyramid, a triangular pyramid and a polygonal pyramid; wherein the base of the cone, pyramid, triangular pyramid or polygonal pyramid is attached or integrally formed with the sharp tip section of the microneedle's skeleton. Each possibility represents a separate embodiment of the present invention. According to some embodiments, the skin augmentation composition slides against the leakage stopper and into the treated area concomitantly with extraction of the microneedles from the skin of the subject. In a non-limiting example, the leakage stopper is in the form of a cone, wherein the augmentation composition slides against the cone and into the treated skin upon extraction of the microneedles from the skin. According to some embodiments, extraction of the microneedles from the skin results from pulling the applicator away from the skin of the subject.

Figure 1B:
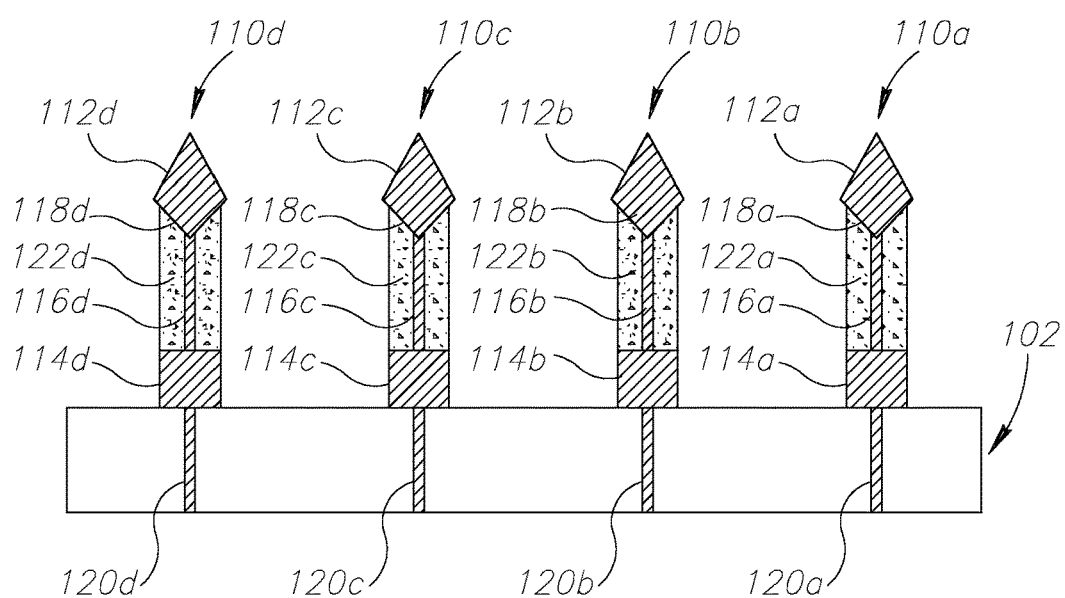
FIG. 1B shows a cross section along line A-A of the applicator of FIG. 1A, according to some embodiments of the invention.

FIG. 1B shows a cross section along line A-A of applicator (100) of FIG. 1A, according to some embodiments of the invention. Substrate (102) of applicator (100) comprises microneedles (110a, 110b, 110c and 110d). According to some embodiments, microneedles (110a, 110b, 110c and 110d) are configured to deliver a composition according to embodiments of the invention to undesired lines, wrinkles, depressed scars or folds of a subject's face. According to the embodiment depicted in FIG. 1B, microneedles (110a, 110b, 110c and 110d) on substrate (102) have substantially the same length. According to other embodiments, microneedles (110a and 110d), situated near the margins of substrate (102), may have the same length while microneedles (110b and 110c), situated at the center of substrate (102) may have the same length and be longer than microneedles (110a and 110d). Microneedle (110a) includes a skeleton comprising three sections: a sharp tip section (112a) configured to penetrate the skin of a subject, a base (114a) located on the opposing end of the skeleton, and a middle section (116a) connecting base (114a) and sharp tip section (112a). Base (114a), sharp tip section (112a) and middle section (116a) are attached to each other and/or are integrally formed with each other. Each possibility represents a separate embodiment of the present invention. Bases (114a, 114b, 114c and 114d) of microneedles (110a, 110b, 110c and 110d) are in the form of a cylinder but may have other shapes, such as, but not limited to a rectangular box, a cuboid, a triangular box, a polygonal box and the like. Base (114a) is attached to or integrally formed with substrate (102a). Each possibility represents a separate embodiment of the present invention. The skeleton of microneedle (110a) further comprises leakage stopper (118a) in the form of a cone, situated in between sharp tip section (112a) and middle section (116a).

It is to be noted that leakage stoppers (118a, 118b, 118c and 118d) of microneedles (110a, 110b, 110c and 110d) are not limited to the form of a cone and may have forms such as, but not limited to, a cone, a pyramid, a triangular pyramid, a polygonal pyramid and the like. Leakage stopper (118a) is integrally formed with sharp tip section (112a) such that the base of the cone forming leakage stopper (118a) is integrally formed with the base of the cone forming sharp tip section (112a). Middle section (116a) is in the form of a longitudinal core extending substantially from the center of sharp tip section (112a) to the center of base (114a). Microneedle (110a) further comprises skin augmentation composition (122a) surrounding middle section (116a). Skin augmentation composition (122a) together with middle section (116a) constitutes the middle part of microneedle (110a). Leakage stopper (118a) is configured to prevent leakage of skin augmentation composition (122a) following extraction of microneedle (110a) from the skin of a subject.

It is to be understood that bases (114*b*, 114*c*, 114*d*), sharp tip sections (112*b*, 112*c*, 112*d*), middle sections (116*b*, 116*c*, 116*d*), leakage stoppers (118*b*, 118*c*, 118*d*) and augmentation compositions (122*b*, 122*c*, 122*d*) of microneedles (110*b*, 110*c*, 110*d*), respectively, and substrate (102) relate to each other essentially as described for the corresponding elements of microneedle (110*a*).

Middle section (116*a*) sends extension (120*a*) through base (114*a*) and into substrate (102). Middle part (116*a*) and extension (120*a*) are perpendicular to base (114*a*) and substrate (102). According to some embodiments, the perpendicular insertion of middle section (116*a*) and extension (120*a*) into base (114*a*) and substrate (102), respectively, confers stability to microneedle (110*a*). According to the embodiment depicted in FIG. 1B, extension (120*d*) of microneedle (110*d*) is thicker than extensions (120*b* and 120*c*) of microneedles (110*b* and 110*c*) which are in turn thicker than extension (120*a*) of microneedle (110*a*). According to some embodiments, different microneedles within the same applicator comprise extensions having different thickness levels. According to some embodiments, a microneedle comprising a thick extension is more stable than a microneedle than a thin extension. As used herein, a stable microneedle refers to a microneedle firmly attached to and/or integrally formed with the substrate.

Figure 2B:
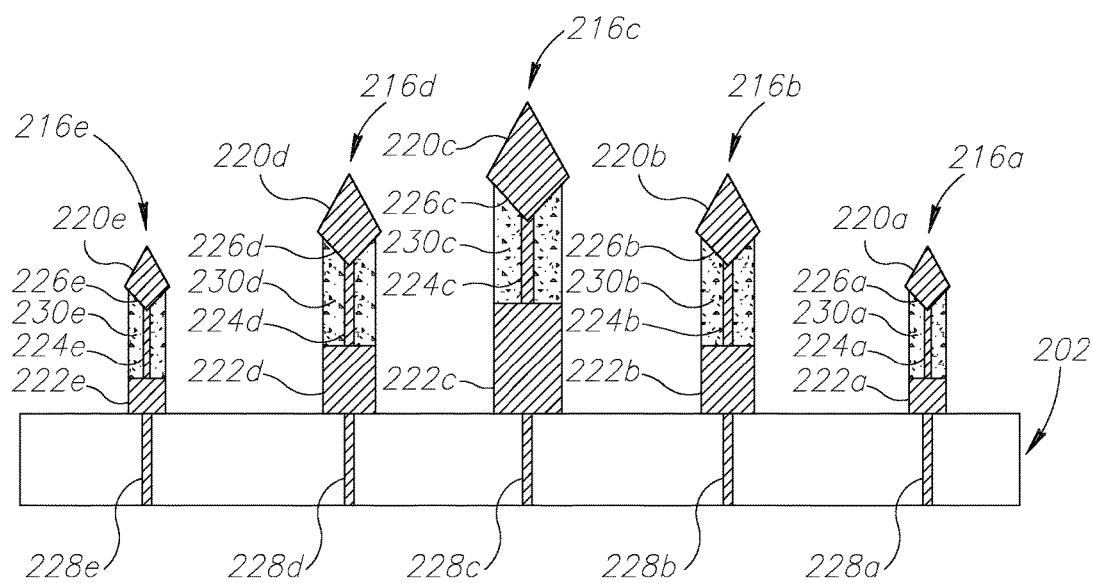
FIG. 2B shows a cross section along line B-B of the applicator of FIG. 2B, according to some embodiments of the invention.

FIG. 2B shows a cross section along line B-B of applicator (200) of FIG. 2, according to some embodiments of the invention. Substrate (202) comprises microneedles (216*a*, 216*b*, 216*c*, 216*d*, 216*e*). According to some embodiments, microneedles (216*a*, 216*b*, 216*c*, 216*d*, 216*e*) are configured to deliver skin augmentation composition (230*a*, 230*b*, 230*c*, 230*d*, 230*e*) to undesired lines, wrinkles, depressed scars or folds of a subject's face. According to some embodiments, microneedles (216*a* and 216*e*) are shorter than microneedles (216*b* and 216*d*) which are in turn shorter than microneedle (216*c*). According to some embodiments, microneedles (216*a* and 216*e*) are configured to deliver augmentation composition (230*a* and 230*e*) to the ends and/or margins of a wrinkle, line or the like to be treated, microneedle (216*c*) is configured to deliver augmentation composition (230*c*) to the center/deep region of the a wrinkle, line or the like to be treated. Each possibility represents a separate embodiment of the present invention. According to some embodiments, applicators configured to be applied to areas having thinner skin (such as, but not limited to, near the eyes) comprise shorter microneedles than applicators configured to be applied to areas having thicker skin (such as, but not limited to, nasolabial folds).

According to some embodiments, microneedle (216*a*) includes a skeleton comprising three sections: a sharp tip section (220*a*) configured to penetrate the skin of a subject, a base (222*a*) located on the opposing end of the skeleton, and a middle section (224*a*) connecting base (222*a*) and sharp tip section (220*a*). Base (222*a*), sharp tip section (220*a*) and middle section (224*a*) are attached to each other and/or are integrally formed with each other. Each possibility represents a separate embodiment of the present invention. Bases (222*a*, 222*b*, 222*c*, 222*d*, 222*e*) of microneedles (216*a*, 216*b*, 216*c*, 216*d*, 216*e*) are in the form of a cylinder but may have other shapes, such as, but not limited to a rectangular box, a cuboid, a triangular box, a polygonal box and the like. Base (222*a*) is attached to or integrally formed with substrate (202). Each possibility represents a separate embodiment of the present invention. The skeleton of each one of microneedles (216*a*) further comprises leakage stopper (226*a*) in the form of a cone, situated in between sharp tip section (220*a*) and middle section (224*a*). It is to be noted that leakage stoppers (226*a*, 226*b*, 226*c*, 226*d*, 226*d*) of microneedles (216*a*, 216*b*, 216*c*, 216*d*, 216*e*) are not limited to the form of a cone and may have forms such as, but not limited to, a cone, a pyramid, a triangular pyramid, a polygonal pyramid and the like. Leakage stopper (226*a*) is integrally formed with sharp tip section (220*a*) such that the base of the cone forming leakage stopper (226*a*) is integrally formed with the base of the cone forming sharp tip section (220*a*). Middle section (224*a*) is in the form of a longitudinal core extending substantially from the center of sharp tip section (220*a*) to the center of base (222*a*). Microneedles (216*a*) further comprises skin augmentation composition (230*a*) surrounding middle section (224*a*). Skin augmentation composition (230*a*) together with middle section (224*a*) constitutes the middle part of microneedle (216*a*). Leakage stopper (226*a*) is configured to prevent leakage of skin augmentation composition (230*a*) following extraction of microneedles (216*a*) from the skin of a subject. Middle section (224*a*) sends extension (228*a*) through base (222*a*) and into substrate (202). Middle part (224*a*) and extension (228*a*) are perpendicular to base (222*a*) and substrate (202). According to some embodiments, the perpendicular insertion of middle section (224*a*) and extension (228*a*) into base (222*a*) and substrate (202), respectively, confers stability to microneedle (216*a*).

It is to be understood that bases (222*b*, 222*c*, 222*d*, 222*e*), sharp tip sections (220*b*, 220*c*, 220*d*, 220*e*), middle sections (224*b*, 224*c*, 224*d*, 224*e*), leakage stoppers (226*b*, 226*c*, 226*d*, 226*e*), extensions (228*b*, 228*c*, 228*d*, 228*e*) and augmentation compositions (230*b*, 230*c*, 230*d*, 230*e*) of microneedles (216*b*, 216*c*, 216*d*, 216*e*), respectively, and substrate (202) relate to each other essentially as described for the corresponding elements of microneedle (216*a*).

Base (222*c*) of microneedle (216*c*) is longer than bases (222*b* and 222*d*) of microneedles (216*b* and 216*d*), which are in turn longer than bases (222*a* and 222*e*) of microneedles (216*a* and 216*e*). According to some embodiments, the applicator comprises microneedles having bases of various lengths. According to some embodiments, long microneedle bases, such as base (222*c*) of microneedle (216*c*), ensure delivery of augmentation composition such as (230*c*) to deep skin layers or subcutaneously without delivery to shallower layers of the skin. Each possibility represents a separate embodiment of the present invention.

FIG. 4A schematically shows microneedle (400*a*) on substrate (401*a*), according to some embodiments of the invention. According to some embodiments, microneedle (400*a*) includes a skeleton comprising three sections: a sharp tip section (402*a*) configured to penetrate the skin of a subject located at the proximal-most end of the skeleton, a base (404*a*) located on the opposing end of the skeleton, and a middle section (406*a*) connecting base (404*a*) and sharp tip section (402*a*). Base (404*a*), sharp tip section (402*a*) and middle section (406*a*) are attached to each other and/or are integrally formed with each other. Each possibility represents a separate embodiment of the present invention. Base (404*a*) is in the form of a cylinder but may have other shapes, such as, but not limited to a rectangular box, a cuboid, a triangular box, a polygonal box and the like. Base (404*a*) is attached to or integrally formed with substrate (401*a*). Each possibility represents a separate embodiment of the present invention. The skeleton of microneedle (400*a*) further comprises leakage stopper (408*a*) in the form of a cone, situated in between sharp tip section (402*a*) and middle section (406*a*). Leakage stopper (408) is in the form of a cone but may have different forms such as, but not limited to a pyramid, triangular pyramid and the like.

Sharp tip section (402a) is in the form of a cone, but may have a different form, such as, but not limited to a pyramid, a triangular pyramid or a polygonal pyramid. Leakage stopper (408a) is integrally formed with sharp tip section (402a) such that the base of the cone forming leakage stopper (408a) is integrally formed with the base of the cone forming sharp tip section (402a). Middle section (406a) is in the form of a longitudinal core extending substantially from the center of sharp tip section (402a) to the center of base (404a). Middle section (406a) sends extension (410a) through base (404a) and into substrate (401a). Middle part (116a) and extension (410a) are perpendicular to base (404a) and substrate (401a). According to some embodiments, the perpendicular insertion of middle section (406a) and extension (410a) into base (404a) and substrate (401a), respectively, confers stability to microneedle (400a). Microneedle (400a) further comprises skin augmentation composition (412a) surrounding middle section (406a). The skin augmentation composition (412a) together with middle section (406a) constitutes the middle part of microneedle (400a). Leakage stopper (408a) is configured to prevent leakage of skin augmentation composition (412a) following extraction of microneedle (400a) from the skin of a subject. According to some embodiments, skin augmentation composition (412a) comprises hydroxyapatite beads of about 40 µm and polyethylene glycol having a molecular weight of 20-50 kDa.

FIG. 4D shows cross section (414) along line C-C of the middle part of microneedle (400a). Cross section (414) shows middle part (406a) of the microneedle's skeleton and skin augmentation composition (412a). Line (d1) represents the diameter of cross section (414). It is to be noted that line (d1) represents the diameter of the middle part of microneedle (400a) at its widest part. FIG. 4E shows cross section (418) along line D-D of the sharp tip section (402a). Line (d2) represents the diameter of cross section (418). It is to be noted that line (d2) represents the diameter of sharp tip section (402a) at its widest part. As can be seen in FIG. 4D and FIG. 4E, according to the embodiment depicted in FIG. 4A, diameter (d2) of sharp tip section (402) is larger than diameter (d1) of the middle part of microneedle (400). According to some embodiments, a microneedle having a sharp tip section with a larger diameter than the diameter of the microneedle's middle part enables insertion of the microneedle into the skin of a subject without spillage of the skin augmentation composition outside the body.

FIG. 4B and FIG. 4C depict microneedles (400b) and (400c), respectively, according to some embodiments of the invention. Sharp tip sections (402b, 402c), middle sections (406b, 406c), leakage stoppers (408b, 408c), extensions (410b, 410c) and augmentation compositions (412b, 412c) of microneedles (400b, 400c), respectively, and substrates (401b, 401c) relate to each other essentially as described for the corresponding elements of microneedle (400a). Microneedles (400b and 400c) are of the same length of microneedle (400a) depicted in FIG. 4A.

Base (404b) of microneedle (400b) and base (404c) of microneedle (400c) have lengths h2 and h3, respectively, which are higher than length h1 of base (404a) depicted in FIG. 4A as part of microneedle (400a). Length h3 of Base (404c) is higher than length h2 of base (404b). According to some embodiments, a longer skeleton base is configured to prevent delivery of skin augmentation composition to shallow skin layers, such as, but not limited to, the epidermis. According to some embodiments, different skin areas require different lengths of microneedle bases due to differences in thickness of skin layers, such as, but not limited to, the epidermis. In a non-limiting example, microneedle (400c) may be used to treat a skin area having a thick epidermal layer, while microneedles (400a) or (400b) may be used to treat a skin area having a thinner epidermal layer.

Figure 5A:
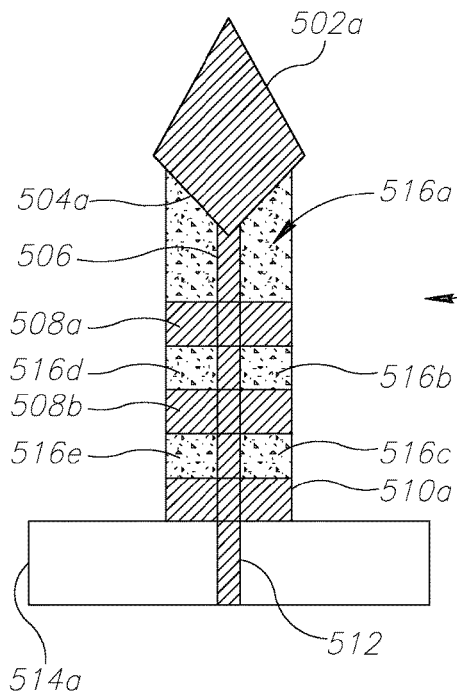
FIGS. 5A-C schematically show microneedles, according to some embodiments of the invention.
Figure 5B:
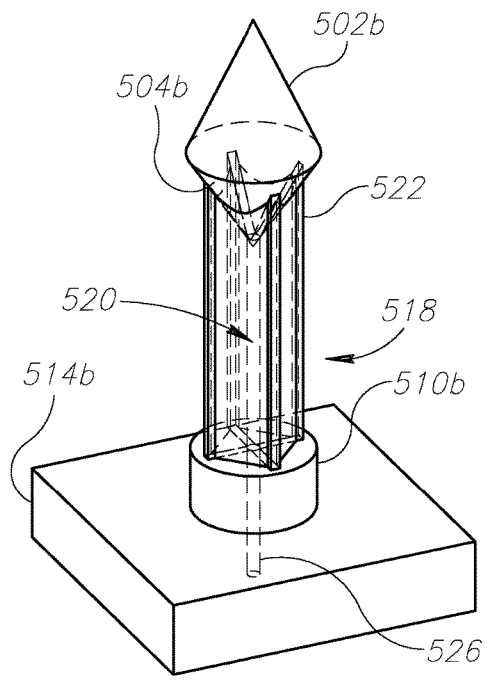
Figure 5B:
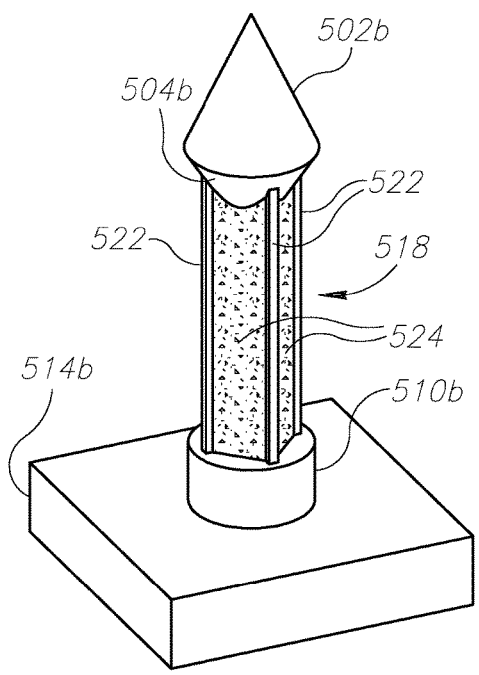
Figure 5C:
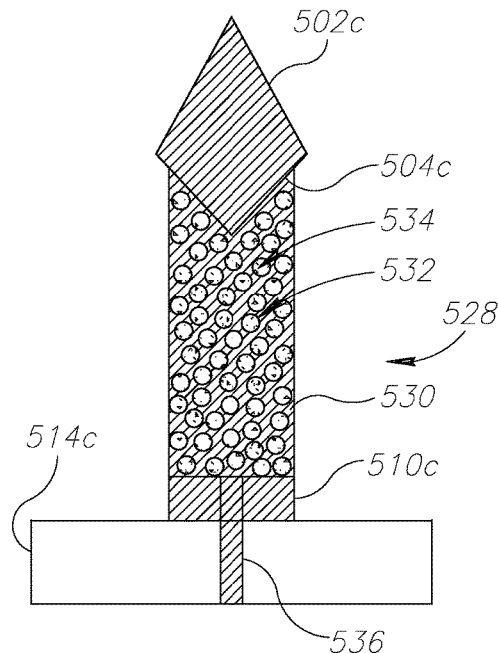

FIGS. 5A-5C show different microneedles, according to various embodiments of the present invention. FIG. 5A shows microneedle (500) on substrate (514a), according to some embodiments of the invention. Microneedle (500) comprises a skeleton composed of: sharp tip section (502a) integrally formed with leakage stopper (504a), base (510a) and a middle section composed of longitudinal core (506) and discs (508a, 508b) around longitudinal core (506). Longitudinal core (506) is attached to or integrally formed with leakage stopper (504a). Each possibility represents a separate embodiment of the present invention. Microneedle (500) further comprises skin augmentation composition (516a, 516b, 516c, 516d, 516e) surrounding longitudinal core (506), in between discs (508a, 508b) and between disc (508b) and base (510a). Longitudinal core (506) sends extension (512) through base (510a) and into substrate (514a). Longitudinal core (506) is attached to or integrally formed with base (510a).

It is to be understood that substrates (514b, 514c), as well as sharp tip sections (502b, 502c), leakage stoppers (504b, 504c) and bases (510b, 510c) of microneedles (518 and 528), as depicted in FIGS. 5B, 5B' and 5C, are essentially identical to corresponding elements (514a, 502a, 504a, 510a) of FIG. 5A.

FIG. 5B shows another embodiment of a microneedle according to the present invention. FIG. 5B' shows an internal view of the microneedle of FIG. 5B. The skeleton's middle section of microneedle (518), as shown in FIGS. 5B and 5B', comprises a narrow longitudinal core (520) and several longitudinal flaps (522) extending outwards from longitudinal core (520). Longitudinal flaps (522) are attached to or integrally formed with leakage stopper (504b). Each possibility represents a separate embodiment of the present invention. Longitudinal flaps (522) are attached to or integrally formed with base (510b). Each possibility represents a separate embodiment of the present invention. According to the embodiment depicted in FIG. 5B, skin augmentation composition (524) is situated in between longitudinal flaps (522). As depicted in FIG. 5B', narrow longitudinal core (520) sends narrow extension (526) through base (510b) and into substrate (514b).

The skeleton's middle section of microneedle (528), as shown in FIG. 5C, is composed of a rigid material (530) having a plurality of cavities (532). According to the embodiment depicted in FIG. 5C, skin augmentation composition (534) is situated at least partly within cavities (532). According to some embodiments, rigid material (530) is attached to or integrally formed with base (510c). Each possibility represents a separate embodiment of the present invention. According to some embodiments, rigid material (530) is attached to or integrally formed with leakage stopper (504c). Each possibility represents a separate embodiment of the present invention. Rigid material (530) sends extension (536) through base (510c) and into substrate (514c).

Figure 6A:
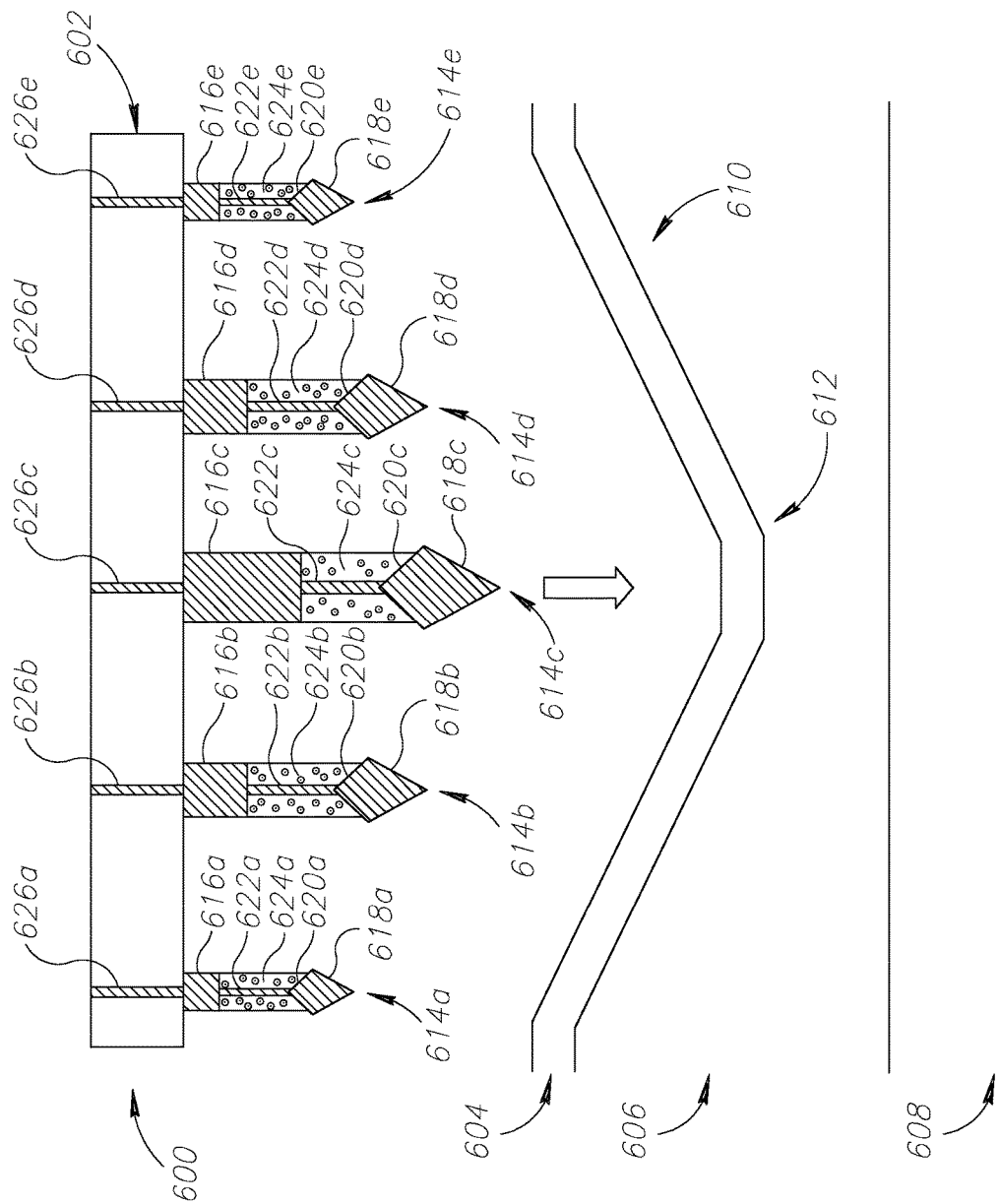

FIGS. 6A-D show treatment of a deep skin line or deficiency using the applicator of the invention, according to several embodiments. As depicted in FIG. 6A, applicator (600) is positioned over and moved towards skin deficiency (610). Skin deficiency (610) may be a deficiency in skin, sub-cutaneous layers or a combination thereof. Applicator (600) comprises substrate (602) and microneedles (614a, 614b, 614c, 614d, 614e). Microneedles (614a and 614e) are of the same length and are shorter than microneedles (614*b* and 614*d*), which have the same length and are in turn shorter than microneedle (614*c*). Applicator (600) is positioned over skin deficiency (610) such that longer microneedles (614*b*, 614*c*, 614*d*), located substantially in the center of substrate (602), are positioned over the deepest point (612) of skin deficiency (610). Shorter microneedles (614*a* and 614*e*) are positioned over the shallower parts of skin deficiency (610). According to some embodiments, long microneedles (614*c*) are configured to deliver skin augmentation composition (624*c*) to deeper skin or subcutaneous layers, such as, but not limited to, the hypodermis (608). According to some embodiments, an applicator such as applicator (600) having microneedles (614*a*, 614*b*, 614*c*, 614*d*, 614*e*) of different lengths is configured for a more uniform augmentation of a deep and/or non-uniformly shaped skin deficiency such as skin deficiency (610). Each possibility represents a separate embodiment of the present invention. According to some embodiments, skin deficiency (610) is a nasolabial fold.

Each one of microneedles (614*a*, 614*b*, 614*c*, 614*d*, 614*e*) comprises a skeleton comprising three sections: base (616*a*, 616*b*, 616*c*, 616*d*, 616*e*), sharp tip section (618*a*, 618*b*, 618*c*, 618*d*, 618*e*) configured to penetrate the skin of a subject and integrally formed with leakage stopper (620*a*, 620*b*, 620*c*, 620*d*, 620*e*), and middle section (622*a*, 622*b*, 622*c*, 622*d*, 622*e*) connecting base (616*a*, 616*b*, 616*c*, 616*d*, 616*e*) and leakage stopper (620*a*, 620*b*, 620*c*, 620*d*, 620*e*). Each one of middle sections (622*a*, 622*b*, 622*c*, 622*d*, 622*e*) sends extension (626*a*, 626*b*, 626*c*, 626*d*, 626*e*) through bases (616*a*, 616*b*, 616*c*, 616*d*, 616*e*) and into substrate (602). Each one of microneedles (614*a*, 614*b*, 614*c*, 614*d*, 614*e*) further comprises skin augmentation composition (624*a*, 624*b*, 624*c*, 624*d*, 624*e*) surrounding middle section (622*a*, 622*b*, 622*c*, 622*d*, 622*e*). Leakage stoppers (620*a*, 620*b*, 620*c*, 620*d*, 620*e*) are configured to prevent leakage of skin augmentation composition (624*a*, 624*b*, 624*c*, 624*d*, 624*e*) following extraction of microneedles (614*a*, 614*b*, 614*c*, 614*d*, 614*e*) from the skin of a subject.

Bases (616*a* and 616*e*) of microneedles (614*a* and 616*e*), respectively, are of the same length and are shorter than bases (616*b* and 616*d*) of microneedles (614*b* and 616*d*) which have the same length and are in turn shorter than base (616*c*) of microneedle (614*c*). Base (616*c*) is long and configured to prevent delivery of skin augmentation composition (624*c*) to the epidermis (604) and dermis (606) layer, thus microneedle (614*c*) delivers skin augmentation composition (624*c*) to deep layers, such as, but not limited to, the hypodermis (608). Bases (616*a*, 616*b*, 616*d*, 616*e*) are configured to prevent delivery of skin augmentation composition (624*a*, 624*b*, 624*d*, 624*e*) to the epidermis (604) and superficial layers, thus microneedles (614*a*, 614*b*, 614*d*, 614*e*) deliver skin augmentation composition (624*a*, 624*b*, 624*d*, 624*e*) to sub-epidermal layers, such as, but not limited to, the dermis (606). According to some embodiments, the length of the microneedle's base is directly correlated to the thickness of the epidermis and/or other superficial layers to be penetrated by the microneedle. Each possibility represents a separate embodiment of the present invention. According to some embodiments, the length of the microneedle's base is directly correlated to the depth of the dermal or sub-dermal layer to which the composition of the invention is to be delivered. Each possibility represents a separate embodiment of the present invention. According to some embodiments, a microneedle configured to deliver the composition of the invention to a subdermal layer comprises a longer microneedle base than a microneedle configured to deliver the composition to the dermis. According to some embodiments, the length of the microneedle's base is at least as long as the thickness of the epidermis and/or other layers to be penetrated by the microneedle. According to some embodiments, the microneedle's base is longer than the thickness of the epidermal layer to be penetrated by the microneedle. According to some embodiments, the applicator comprises microneedles having different lengths of microneedle base in correlation to the position of the microneedle on the substrate.

FIG. 6B depicts applicator (600) following application to skin deficiency (610). As can be seen in FIG. 6B, substrate (602) is flexible and, following application, conforms to the contours of skin deficiency (610). Following application, microneedles (614*a*, 614*b*, 614*c*, 614*d*, 614*e*) penetrate through the epidermis (604). Microneedles (614*a*, 614*b*, 614*d*, 614*e*) penetrate into the dermis (606), while longer microneedle (614*c*) penetrates into lower layer (608), such as, but not limited to, the hypodermis. The length of bases (616*a*, 616*b*, 616*d*, 616*e*) is longer than the thickness of epidermis (604), thus preventing delivery of skin augmentation composition (624*a*, 624*b*, 624*d*, 624*e*) to the epidermis (604). Base (616*c*) is as long as the thickness of epidermis (604) and dermis (606) together, thus preventing delivery of skin augmentation composition (624*c*) to the epidermis (604) and the dermis (606).

Figure 6C:
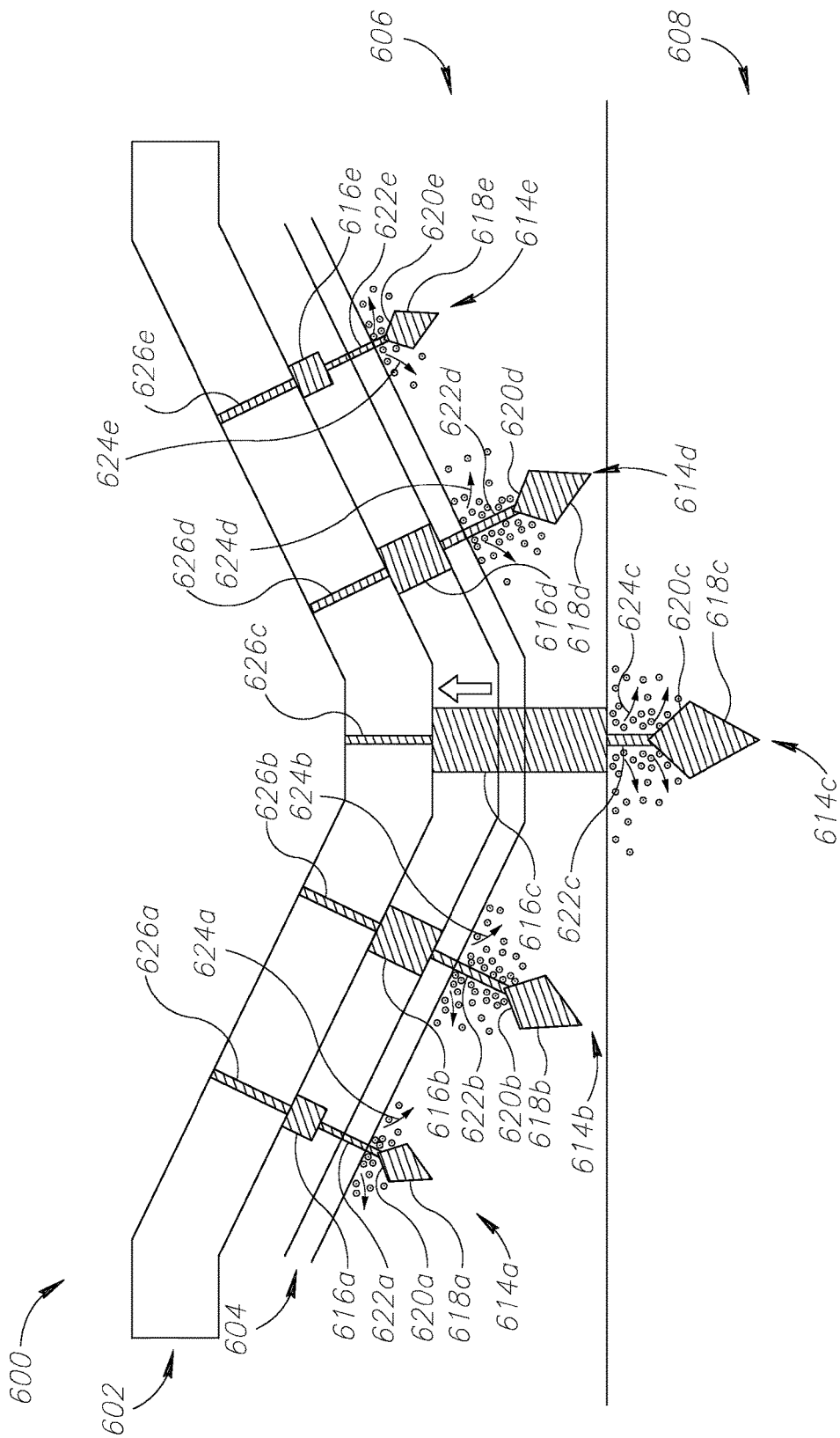

FIG. 6C depicts applicator (600) in the process of being removed from skin deficiency (610) following treatment according to some embodiments of the present invention. As can be seen in FIG. 6C, during extraction of microneedles (614*a*, 614*b*, 614*c*, 614*d*, 614*e*) from the skin, at least part of skin augmentation composition (624*a*, 624*b*, 624*c*, 624*d*, 624*e*) slides over leakage stoppers (620*a*, 620*b*, 620*c*, 620*d*, 620*e*) of microneedles (614*a*, 614*b*, 614*c*, 614*d*, 614*e*) and into the skin of the subject. According to some embodiments, only the part of skin augmentation composition (624*a*, 624*b*, 624*c*, 624*d*, 624*e*) that did not undergo biodegradation in the skin of the subject during application slides over leakage stoppers (620*a*, 620*b*, 620*c*, 620*d*, 620*e*) of microneedles (614*a*, 614*b*, 614*c*, 614*d*, 614*e*) and into the skin or sub-cutis of the subject.

Figure 6D:
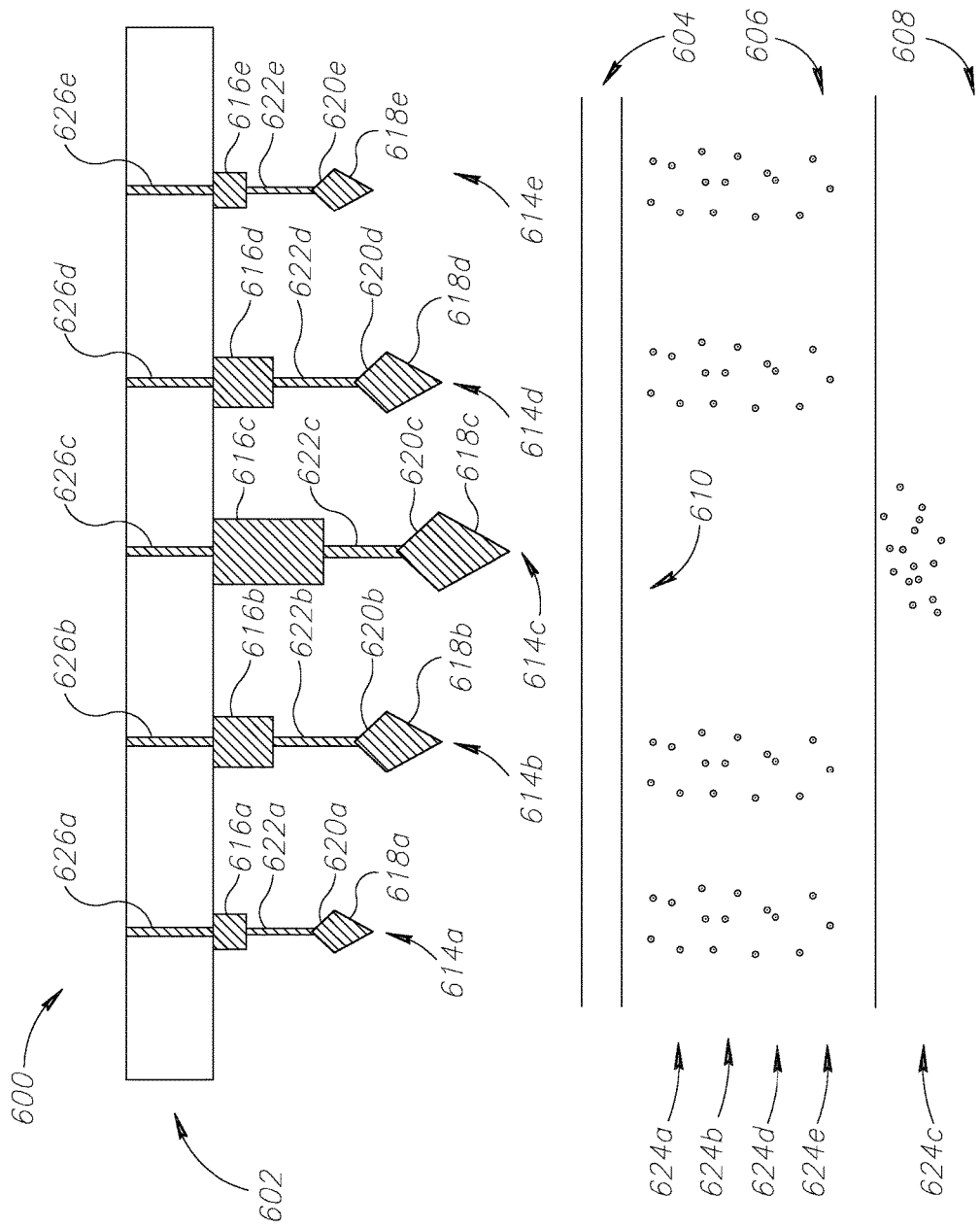

As can be seen in FIG. 6D, after applicator (600) has been extracted from the skin of the subject, augmentation composition (624*a*, 624*b*, 624*d*, 624*e*) remains within the dermis (606) and augmentation composition (624*c*) remains within the hypodermis (608) such that skin deficiency (610) has been augmented. Following extraction of applicator (600) from the skin of the subject, substrate (602) regains its original shape and comprises only the skeletons of microneedles (614*a*, 614*b*, 614*c*, 614*d*, 614*e*).

Figure 7A:
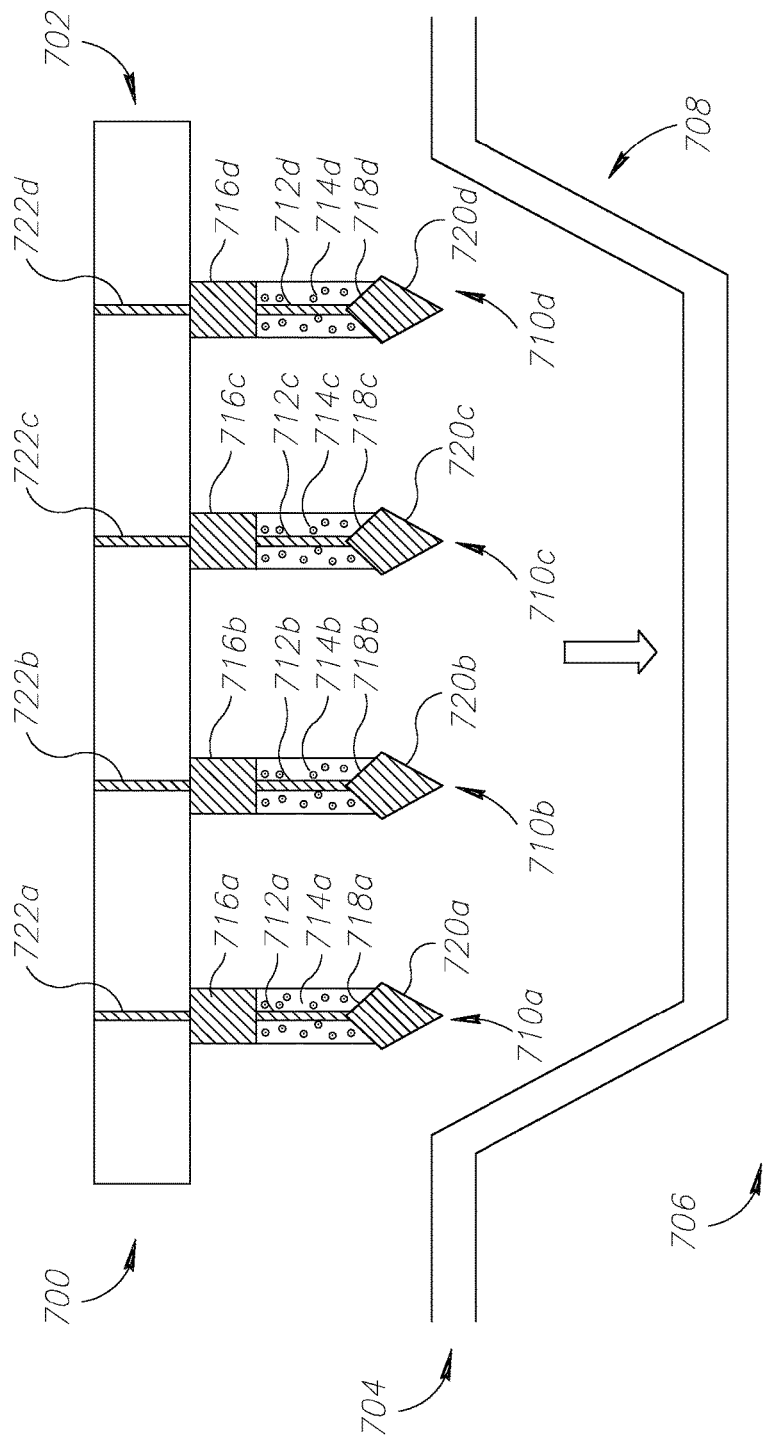
FIGS. 7A-D schematically show application of an applicator to a shallow skin line or deficiency, according to some embodiments of the invention.

FIGS. 7A-D show treatment of a shallow skin line or deficiency using the applicator of the invention, according to several embodiments. As depicted in FIG. 7A, applicator (700) is positioned over and moved towards skin deficiency (708). Applicator (700) comprises substrate (702) and microneedles (710*a*, 710*b*, 710*c*, 710*d*). Microneedles (710*a*, 710*b*, 710*c*, 710*d*) of applicator (700) are all of substantially the same length and are configured to deliver augmentation composition (714*a*, 714*b*, 714*c*, 714*d*) to the dermis (706) of the treated subject.

Each one of microneedles (710*a*, 710*b*, 710*c*, 710*d*) comprises a skeleton comprising three sections: base (716*a*, 716*b*, 716*c*, 716*d*), sharp tip section (720*a*, 720*b*, 720*c*, 720*d*) configured to penetrate the skin of a subject and integrally formed with leakage stopper (718*a*, 718*b*, 718*c*, 718*d*), and middle section (712*a*, 712*b*, 712*c*, 712*d*) connecting base (716*a*, 716*b*, 716*c*, 716*d*) and leakage stopper (718*a*, 718*b*, 718*c*, 718*d*). Each one of middle sections (712*a*, 712*b*, 712*c*, 712*d*) sends extension (722*a*, 722*b*, 722*c*, 722*d*) through bases (716*a*, 716*b*, 716*c*, 716*d*) and into substrate (702). Each one of microneedles (710*a*, 710*b*, 710*c*, 710*d*) further comprises skin augmentation composition (714*a*, 714*b*, 714*c*, 714*d*) surrounding middle section (712*a*, 712*b*, 712*c*, 712*d*). Leakage stoppers (718*a*, 718*b*, 718*c*, 718*d*) are configured to prevent leakage of skin augmentation composition (714*a*, 714*b*, 714*c*, 714*d*) following extraction of microneedles (710*a*, 710*b*, 710*c*, 710*d*) from the skin of a subject.

Figure 7B:
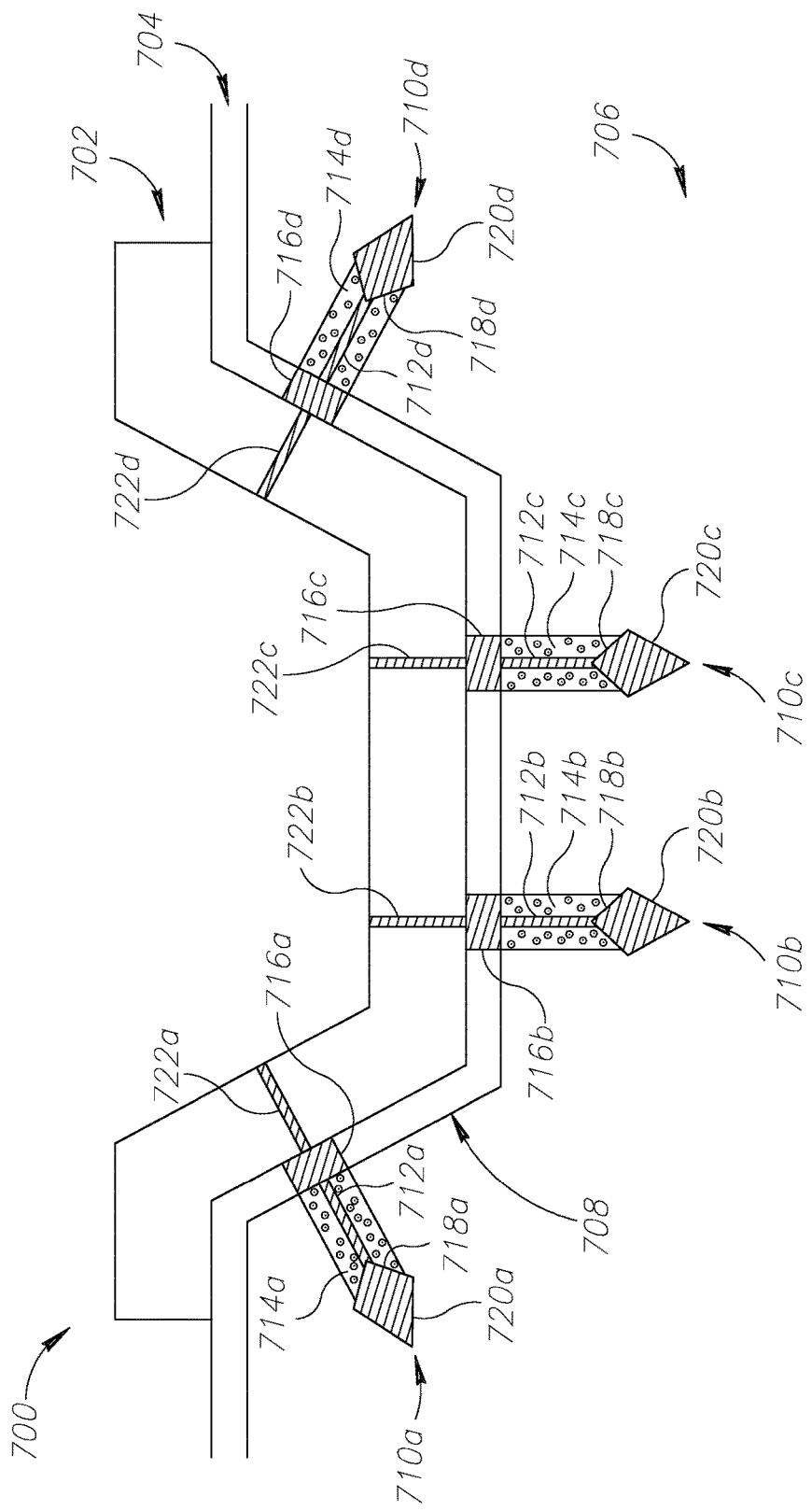

FIG. 7B depicts applicator (700) following application to the skin deficiency (708). As can be seen in FIG. 7B, substrate (702) is flexible and, following application, conforms to the contours of skin deficiency (708). Following application, microneedles (710*a*, 710*b*, 710*c*, 710*d*) penetrate through the epidermis (704) and enter into the dermis (706). According to some embodiments, base (716*a*, 716*b*, 716*c*, 716*d*) of microneedles (710*a*, 710*b*, 710*c*, 710*d*) is as long as the thickness of epidermis (704), thus preventing delivery of augmentation composition (714*a*, 714*b*, 714*c*, 714*d*) to the dermis (704).

Figure 7C:
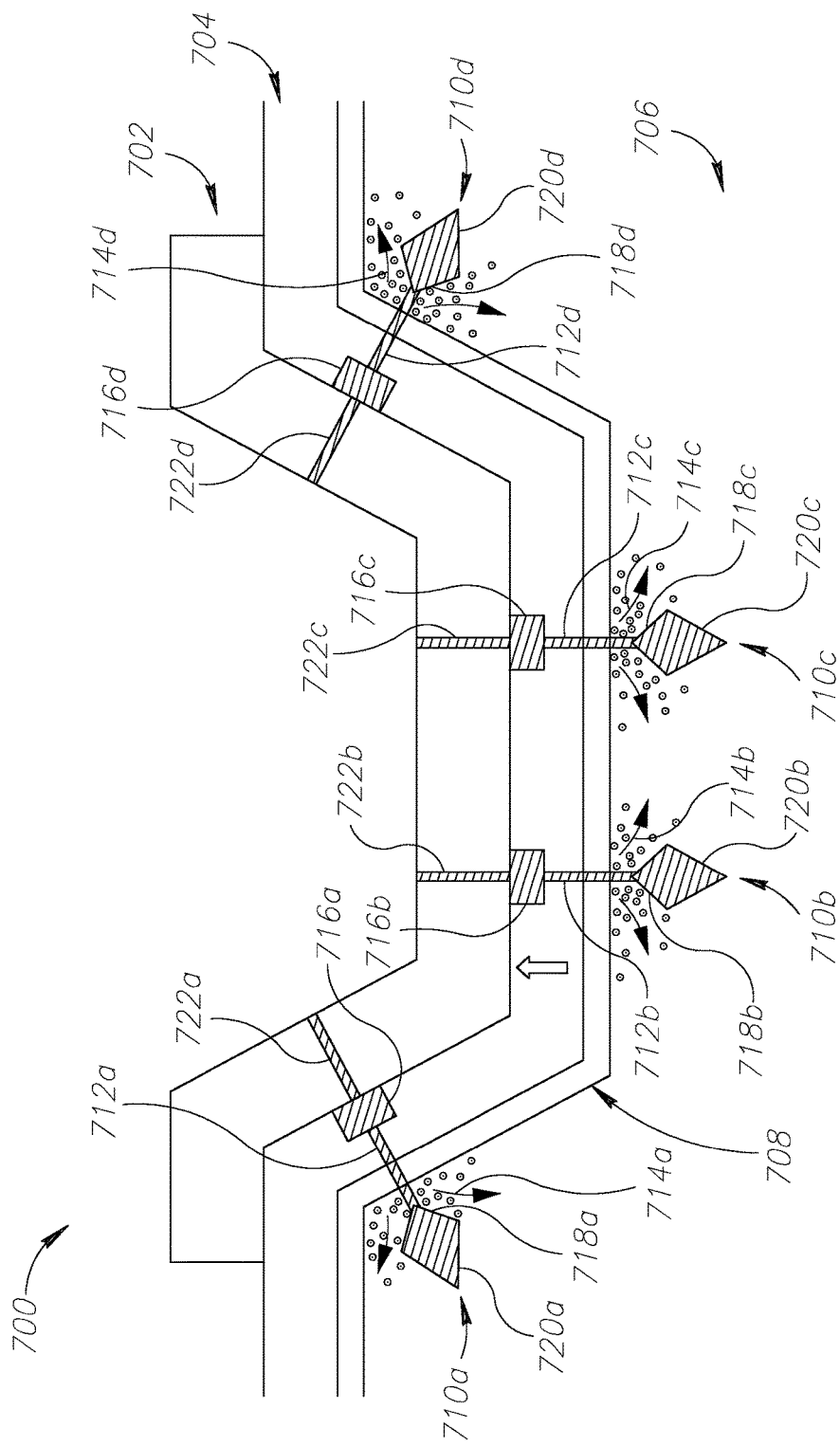

FIG. 7C depicts applicator (700) in the process of being removed from skin deficiency (708) following treatment according to some embodiments of the present invention. As can be seen in FIG. 7C, during extraction of microneedles (710*a*, 710*b*, 710*c*, 710*d*) from the skin, at least part of augmentation composition (714*a*, 714*b*, 714*c*, 714*d*) slides over leakage stopper (718*a*, 718*b*, 718*c*, 718*d*) of microneedles (710*a*, 710*b*, 710*c*, 710*d*) and into the dermis (706).

Figure 7D:
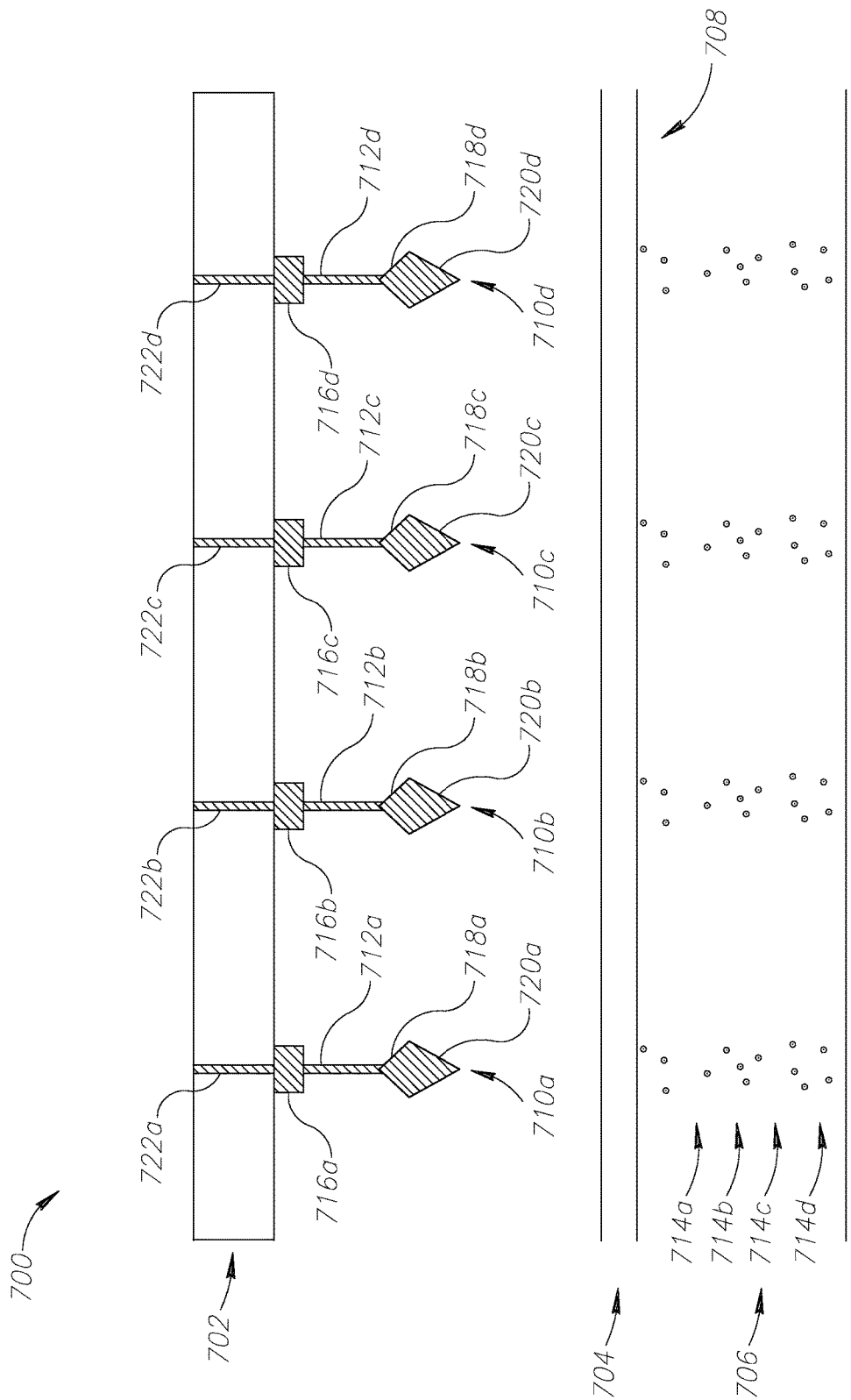

As can be seen in FIG. 7D, after applicator (700) has been extracted from the skin of the subject, at least part of augmentation composition (714*a*, 714*b*, 714*c*, 714*d*) remains within the dermis (706) such that skin deficiency (708) has been augmented. According to some embodiments, only the biocompatible ceramic material that was present in composition (714*a*, 714*b*, 714*c*, 714*d*) remains within the dermis (706). Following extraction of applicator (700) from the skin of the subject, substrate (702) regains its original shape and comprises only the skeletons of microneedles (710*a*, 710*b*, 710*c*, 710*d*).

FIGS. 8A-E depict a manufacturing procedure for microneedles, according to some embodiments of the present invention. As shown in FIG. 8A, first half-mold (800) is loaded with a microneedle skeleton (801) comprising sharp tip section (802), leakage stopper (804), middle section (806), base (808) and extension (810). Sharp tip section (802) may be attached to or integrally formed with leakage stopper (804). According to some embodiments, extension (810) is the direct continuation of middle section (806) protruding through base (808). First half-mold (800) is configured to delineate half of the middle part of the final needle to be produced. According to the embodiment depicted in FIG. 8A only base (808) and leakage stopper (804) of microneedle skeleton (801) are in direct contact with first half-mold (800). According to some embodiments, extension (810), sharp tip section (802) and part of leakage stopper (804) protrude from first half-mold (800). According to some embodiments, at least part of base (808) protrudes from first half-mold (800). First half-mold (800) is depicted having a rectangular shape but may have any shape which best suits production of microneedles according to the depicted embodiments. As shown in FIG. 8B, augmentation composition (812) is deposited on microneedle skeleton (801) such that it covers middle section (806) and part of leakage stopper (804). As shown in FIG. 8C, second half-mold (814) is fitted onto first half-mold (800) and microneedle skeleton (801) onto which augmentation composition has been deposited. When fitted around microneedle skeleton (801) onto which augmentation composition had been deposited, first half-mold (800) and second half-mold (814) are configured to delineate the middle part of the microneedle such that the augmentation composition in the resulting microneedle will surround middle section (806) and at least part of leakage stopper (804). First half-mold (800) and second half-mold (814) are configured to shape the middle part of the produced microneedle to a desired shape. According to some embodiments, first half-mold (800) and second half-mold (814) are configured to partly interlock into each other. As seen in FIG. 8D, augmentation composition (812) which defines the middle part of the produced microneedle, is in the shape of a cylinder following removal of second half-mold (814), but may be in other shapes, such as a polygonal box, as provided by first half-mold (800) and second half-mold (814). FIG. 8E depicts the final microneedle as produced according to the embodiments of FIGS. 8A-E. Extension (810) may be inserted into a substrate of an applicator according to the present invention. Extension (810) may be cut to fit a substrate according to the present invention, either before or after being inserted into the substrate.

According to other embodiments (not shown), first half-mold (800) is loaded with microneedle skeleton (801) followed by deposition of augmentation composition (812) onto part of middle section (806) and leakage stopper (804) such that only the parts of middle section (806) and leakage stopper (804) that are within first half-mold (800) are filled with augmentation composition (812). Excess augmentation composition (812) may be removed. After augmentation composition (812) that has been deposited within first half-mold (800) has dried, additional augmentation composition may be added on top of the dried augmentation composition followed by fitting of second half-mold (814) onto first half-mold (800). After the augmentation composition has fully dried, first half-mold (800) and second half-mold (814) may be removed, resulting in the final microneedle, as depicted in FIG. 8E.

According to another aspect, the present invention provides a method for manufacturing a microneedle for administration of a skin augmentation composition to a skin and/or sub-cutis of a subject, the method comprises: producing a microneedle skeleton of a rigid material, said skeleton comprising: a sharp tip section located on one end of said skeleton, said sharp tip section being configured to penetrate a skin of a subject; a base on an opposing end of said skeleton; and a middle section connecting between said sharp tip section and said base; and depositing a skin augmentation composition on said skeleton such that said composition at least partly surrounds said middle section and a diameter of said sharp tip section is larger than a diameter of said augmentation composition; wherein said composition comprises at least one biocompatible ceramic material.

According to some embodiments, depositing the skin augmentation composition according to the method for manufacturing of the present invention comprises preventing deposition of the skin augmentation composition around the base and sharp tip section.

According to some embodiments, the method for manufacturing of the present invention further comprises placing the microneedle skeleton in a mold prior to depositing the skin augmentation composition, wherein the mold is configured to shape the skin augmentation composition around at least part of the middle section. According to some embodiments, the mold is further configured to prevent deposition of the skin augmentation composition around the base and sharp tip section.

According to some embodiments, the present invention provides a method of manufacturing the microneedles of the invention, the method comprises depositing a skin augmentation composition around at least part of the middle section of the microneedle such that the sharp tip section and the base of the microneedle remain devoid of skin augmentation composition. According to some embodiments, the method of manufacturing further comprises depositing the skin augmentation composition around at least part of a leakage stopper. According to some embodiments, the method of manufacturing comprises loading a microneedle skeleton on a mold such that the mold is configured to shape the skin augmentation composition around at least part of the middle section, and wherein the mold is configured not to deposit the skin augmentation composition around the base and sharp tip section of the microneedle. According to some embodiments, the mold is configured to shape the skin augmentation composition around at least part of the middle section and at least part of the leakage stopper. According to some embodiments, the mold is composed of a plurality of parts, such as, but not limited to a first and a second half molds.

According to another aspect, the present invention provides a method for delivering a skin augmentation composition to a site of skin defect or deficiency, comprising placing at the site an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:

a skeleton made of a rigid material, the skeleton comprises:
  a sharp tip section located on one end of the skeleton, the sharp tip section being configured to penetrate a skin of a subject;
  a base on an opposing end of the skeleton; and
  a middle section connecting between the sharp tip section and the base; and
a skin augmentation composition comprising at least one biocompatible ceramic material, wherein the augmentation composition at least partly surrounds the middle section, such that a diameter of the sharp tip section is larger than a diameter of the augmentation composition.

According to another aspect, the present invention provides a method for filling an undesired fold, wrinkle, line or depressed area in a subject, comprising placing at the site of the fold, wrinkle, line or depressed area an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:

a skeleton made of a rigid material, the skeleton comprises:
  a sharp tip section located on one end of the skeleton, the sharp tip section being configured to penetrate a skin of a subject;
  a base on an opposing end of the skeleton; and
  a middle section connecting between the sharp tip section and the base; and
a skin augmentation composition comprising at least one biocompatible ceramic material, wherein the augmentation composition at least partly surrounds the middle section, such that a diameter of the sharp tip section is larger than a diameter of the augmentation composition.

According to some embodiments, the present invention provides a method for delivering a skin augmentation composition to a site of skin defect or deficiency, comprising placing at the site an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:

a skeleton made of a rigid material, the skeleton comprises:
  a sharp tip section located on one end of the skeleton, the sharp tip section being configured to penetrate a skin of a subject;
  a base on an opposing end of the skeleton; and
  a middle section connecting between the sharp tip section and the base; and
a skin augmentation composition comprising hydroxyapatite beads and/or particles or a salt or derivative thereof, wherein the augmentation composition at least partly surrounds the middle section, such that a diameter of the sharp tip section is larger than a diameter of the augmentation composition. Each possibility represents a separate embodiment of the present invention.

According to some embodiments, undesired fold, wrinkle, line or depressed area refers to undesired fold, wrinkle, line or depressed area in skin, in sub-cutaneous layers or a combination thereof. Each possibility represents a separate embodiment of the present invention. According to some embodiments, skin defect or deficiency refers to a defect or a deficiency in skin, in sub-cutaneous layers or a combination thereof. Each possibility represents a separate embodiment of the present invention. According to some embodiments, the method of the invention comprises placing at the site an applicator configured for administration of a skin augmentation composition to a skin of a subject or to sub-cutis layers of a subject or a combination thereof. Each possibility represents a separate embodiment of the present invention.

According to some embodiments, the present invention provides a method for filling an undesired fold, wrinkle, line or depressed area in a subject, comprising placing at the site of the fold, wrinkle, line or depressed area an applicator configured for administration of a skin augmentation composition to a skin of a subject, the applicator comprising a substrate and an array of microneedles; wherein the substrate has a generally flattened structure having two opposing surfaces, wherein one surface is intended for being placed proximal to the skin of a subject and the other surface facing away from the skin of the subject; wherein the array of microneedles is located on the surface proximal to the skin of the subject, the array comprising a multiplicity of microneedles, wherein each of the microneedles comprises:
- a skeleton made of a rigid material, the skeleton comprises:
  - a sharp tip section located on one end of the skeleton, the sharp tip section being configured to penetrate a skin of a subject;
  - a base on an opposing end of the skeleton; and
  - a middle section connecting between the sharp tip section and the base; and
- a skin augmentation composition comprising hydroxyapatite beads and/or particles and/or a salt or derivative thereof, wherein the augmentation composition at least partly surrounds the middle section, such that a diameter of the sharp tip section is larger than a diameter of the augmentation composition. Each possibility represents a separate embodiment of the present invention.

According to some embodiments, the present invention provides an applicator configured for administration of a skin augmentation composition to a skin and/or sub-cutis of a subject for use in filling an undesired fold, wrinkle, line or depressed area in a subject, the applicator comprising a substrate, wherein the substrate has a generally flattened structure having two opposing surfaces, wherein one surface is intended for being placed proximal to the skin of a subject and the other surface facing away from the skin of the subject; and an array of microneedles, wherein the array of microneedles is located on the surface proximal to the skin of the subject, the array comprising a multiplicity of microneedles, wherein each of the microneedles comprises:
- a skeleton made of a rigid material, the skeleton comprises:
  - a sharp tip section located on one end of the skeleton, the sharp tip section being configured to penetrate a skin of a subject;
  - a base on an opposing end of the skeleton; and
  - a middle section connecting between the sharp tip section and the base; and
- a skin augmentation composition comprising at least one biocompatible ceramic material, wherein the augmentation composition at least partly surrounds the middle section, such that a diameter of the sharp tip section is larger than a diameter of the augmentation composition.

According to some embodiments, the methods of the invention are useful for delivering a skin augmentation composition to a site of skin defect or deficiency. According to some embodiment, the site of skin defect or deficiency is undesired lines, wrinkles folds and the like in the skin of a subject. According to some embodiment, the site of skin defect or deficiency is undesired lines, wrinkles folds and the like in the facial skin of a subject. According to some embodiments, the methods of the invention are useful for filling an undesired fold, wrinkle, line or depressed area in a subject. Each possibility represents a separate embodiment of the present invention.

As used herein, the terms "placing" and "administering" are used interchangeably and refer to locating the applicator of the invention at a desired site. According to some embodiments, following administration, the microneedles penetrate the treatment area and the composition of the invention is delivered to the target site. In a non-limiting example, placing the applicator over a forehead wrinkle results in insertion of the microneedles to the skin of the subject and delivery of the composition of the invention to the dermal and/or sub-dermal layer. According to some embodiments, following placing the applicator on the skin of a subject, the microneedles penetrate the skin and the biodegradable polymer and/or salt undergo biodegradation, thus releasing the biocompatible ceramic which remains in the subject following removal of the applicator.

According to some embodiments, the site of skin defect or deficiency is the site of a scar. According to some embodiments, the terms "treated area" and "treatment area" are interchangeable and refer to a site of skin or sub cutis defect or deficiency, or a combination thereof. Each possibility represents a separate embodiment of the present invention. According to some embodiments, the site of skin or sub cutis defect or deficiency is the site of a depressed scar. Each possibility represents a separate embodiment of the present invention. According to some embodiments, the methods of the invention are useful in augmentation of scars. According to other embodiments, the methods of the invention are useful in filling skin and/or sub cutis scar tissue. Each possibility represents a separate embodiment of the present invention. As used herein, the term "normal skin" refers to a healthy skin and/or a young looking skin.

Non-limiting examples of a site of skin or sub cutis defect or deficiency which may be treated by the applicator of the invention, according to some embodiments, may comprise: delicate forehead, cheek, neck, nasal-bridge and lip wrinkles, nasolabial folds, marionette lines, depressed scars, lips, area of malar bones and a combination thereof. Each possibility represents a separate embodiment of the present invention.

According to some embodiments, the applicator is placed at a site of skin defect or deficiency or at undesired lines, wrinkles folds for at least 1, 2, 3, 5, 6, 7, 8, 9, 10, 11, 12 hours. Each possibility represents a separate embodiment of the present invention. According to some embodiments, the applicator is placed at a site of skin defect or deficiency or at undesired lines, wrinkles folds for at least a full night. As used herein, a full night is between 6-10 hours. According to some embodiments, the applicator is placed at a site of skin defect or deficiency or at undesired lines, wrinkles folds for at least 24 hours. Each possibility represents a separate embodiment of the present invention. According to some embodiments, the applicator is placed at a site of skin defect or deficiency or at undesired lines, wrinkles folds for at least 1, 2, 3, 5, 6, 7 days. Each possibility represents a separate embodiment of the present invention. According to some embodiments, the applicator is placed at a site of skin defect or deficiency or at undesired lines, wrinkles folds for a period of time sufficient for the degradation of the biodegradable carrier. Typically, the applicator is placed at a site of skin defect or deficiency or at undesired lines, wrinkles folds for 24-72 hours.

According to some embodiments, the skin augmentation composition is a slow-releasing skin augmentation composition. As used herein, the term "slow-releasing skin augmentation composition" refers to a composition configured for slow-release of a skin augmentation material and/or of a drug and/or of a toxin. Each possibility represents a separate embodiment of the present invention. In a non-limiting example, the applicator of the invention comprising a slow-releasing skin augmentation material is placed on the face of the subject for several days. According to this non-limiting example, the applicator may induce slow release and slow delivery of the skin augmentation material, thus achieving a more efficient augmentation of the target site.

According to some embodiments, the subject places the applicator of the invention at a desired site. According to some embodiments, the applicator of the invention remains at a desired site for a desired time period through the use of an adhesive. As used herein, the adhesive is inert, biologically compatible and enables easy removal of the applicator of the invention. According to some embodiments, the adhesive is resistant to water. According to some embodiments, the adhesive is located only on part of the inner surface of the substrate. According to some embodiments, the applicator of the invention is resistant to water. According to some embodiments, the applicator is shaped like an adhesive bandage so that it may be placed inconspicuously on the subject's face for a desired time. According to some embodiments, the applicator of the invention may be affixed to the treatment area using external fixation aid such as, but not limited to, a bandage, a handkerchief and the like.

According to some embodiments, the applicator is removed following a desired time period. According to some embodiments, the desired time period depends on the types of microneedles and skin augmentation compositions used in the applicator, on the amount of composition used, on the site of treatment, on the desired effect and a combination thereof. Each possibility represents a separate embodiment of the present invention.

According to some embodiments, following removal of the applicator, at least part of the skin augmentation composition remains at the site of administration while the microneedles' skeletons are removed with the applicator. According to some embodiments, following removal of the applicator, at least part of the biocompatible ceramic remains at the site of administration while the microneedles' skeletons are removed with the applicator.

According to some embodiments, the invention provides a kit comprising at least one of the applicators of the invention and instructions for use of the applicator. According to some embodiments, the applicators, methods and kits of the invention may be used by the subject without needing assistance from a medical care giver. According to some embodiments, the applicators, methods and kits of the invention do not require surgical intervention. According to some embodiments, the methods of the invention are used to fill undesired lines, wrinkles, depressed scars and folds in the face of a subject without use of surgical intervention or needles. Each possibility represents a separate embodiment of the present invention.

According to some embodiments, the method of the invention would have to be repeated several times in order to fill a site of skin defect or deficiency. According to other embodiments, a single use of the applicator of the invention is sufficient to fill a site of skin defect or deficiency. According to some embodiments, the dimensions and/or shape of the site of skin defect or deficiency determine how many times the applicator of the invention would have to be used at the same site of skin defect or deficiency in order to achieve the desired filling. Each possibility represents a separate embodiment of the present invention. In a non-limiting example, a deep and/or wide and/or irregularly shaped skin defect or deficiency may require several repetitions of the method of the invention and/or several applicators of the invention and/or a longer application time for proper filling of the skin defect or deficiency. Each possibility represents a separate embodiment of the present invention.

As used herein, the terms "subject", "a subject in need thereof" and "a patient in need thereof" are used interchangeably and refer to a subject in need of skin or sub cutis augmentation or a combination thereof. According to some embodiments, the subject is a subject having undesired lines, wrinkles, and folds such as, but not limited to, elderly people. According to other embodiments, the subject is a subject having a scar in need of augmentation or filling. In a non-limiting example, a subject is a subject having facial wrinkles which he or she would like to have filled for a healthier and fuller looking facial skin. Of note, a subject may have normal looking skin and wish to use the applicator/method of the invention in order achieve an appearance of fuller skin at a desired area, such as, but not limited to, the cheeks and lips.

As used herein, the term "about" refers to +/−10%, preferably +/−5%, most preferably +/−1%. Each possibility represents a separate embodiment of the present invention.

As used herein, the terms "sub cutaneous" and "sub cutis" are used interchangeably. It is to be understood that the applicator and/or the microneedles of the invention are configured for administration of a skin augmentation composition to skin or to sub-cutaneous layers or to a combination thereof. It is to be understood that the methods of the invention provide augmentation or filling of skin or sub cutaneous layers or a combination thereof.

According to some embodiments, the present invention provides a use of the applicator of the invention for augmentation of skin in a subject in need thereof. According to some embodiments, the present invention provides a use of the applicator of the invention for the filling of an undesired fold, wrinkle, line or depressed area in the skin of a subject in need thereof.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1: Treatment of Delicate Forehead Wrinkles

An applicator comprising a substrate in the form of a strip, comprises an array of microneedles with a skin augmentation composition, such as RADIESSE®. The applicator is placed on a delicate forehead wrinkle and adheres to the subject's face using an adhesive surface comprised in the substrate's surface which is proximal to the skin. The applicator is kept on the skin of the subject for a time period as desired by the user, the caregiver or as instructed by the instructions of the applicator.

Example 2: Treatment of a Nasolabial Fold

An applicator comprising a substrate in the form of a patch is placed on a nasolabial fold. The microneedles of the applicator comprise skeletons having a cylindrical base, a middle section in the form of a cylindrical longitudinal core and a conical sharp tip section. The skeleton further comprises a leakage stopper in the form of a cone, integrally formed with the sharp tip section. The middle section of the skeleton of each microneedle is surrounded by a skin augmentation composition. The skin augmentation composition comprises hydroxyapatite beads (40 µm), polyethylene glycol (40 kDa) and beads of magnesium sulfate. The applicator adheres to the subject's face using an adhesive surface comprised in the substrate's surface which is proximal to the skin. The applicator is kept on the skin of the subject for a time period as desired by the user, the caregiver or as instructed by the instructions of the applicator. The applicator is removed along with the skeletons of the microneedles, while the skin augmentation composition remains within the treated area.

Example 3: Preparation of an Augmentation Composition Comprising Hydroxyapatite

Hydroxyapatite (100 gr) is dispersed in molten polyethylene glycol (PEG 20000) using vigorous stirring. Next, a concentrated magnesium sulfate solution is prepared by dissolving 30 gr of magnesium sulfate in hot water and the hot solution is added to the molten PEG solution with constant mixing. The mixture is mixed until cooled to a paste.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

What we claim is:

1. An applicator configured for administration of a skin augmentation composition to a skin and/or sub cutis of a subject, said applicator comprising:
    a substrate, wherein said substrate has a generally flattened structure having two opposing surfaces, wherein one surface is intended for being placed proximal to the skin of the subject and the other surface facing away from the skin of said subject; and
    an array of microneedles, wherein the array of microneedles is located on the surface proximal to the skin of said subject, said array comprising a plurality of microneedles, wherein each of the microneedles comprises:
   a skeleton made of a rigid material, the skeleton comprising:
      a sharp tip section located on one end of said skeleton, the sharp tip section being configured to penetrate the skin of said subject;
      a base on the opposing end of said skeleton; and
      a middle section connecting between said sharp tip section and the base; and
   a skin augmentation composition comprising at least one biocompatible ceramic material, wherein the augmentation composition at least partly surrounds the middle section, such that a diameter of said sharp tip section is larger than a diameter of said augmentation composition, and wherein a length of said base is equal or greater than a thickness of an epidermis at a treated area, and wherein the base and the sharp tip section of each of the microneedles do not comprise the skin augmentation composition.

2. The applicator of claim 1, wherein said sharp tip section, said base and said middle section are integrally formed.

3. The applicator of claim 1, wherein said skeleton further comprises a leakage stopper; wherein the leakage stopper is situated between said sharp tip section and said middle section; and wherein said leakage stopper is configured to prevent leakage of said augmentation composition from the skin of said subject following extraction of said microneedle from the skin of said subject.

4. The applicator of claim 3, wherein said leakage stopper is integrally formed with said sharp tip.

5. The applicator of claim 1, wherein said base section and/or said middle section has a shape selected from the group consisting of: a cylinder, a rectangular box, a cuboid, a triangular box and a polygonal box; and wherein said tip section has a shape selected from the group consisting of: a cone, a pyramid, a triangular pyramid and a polygonal pyramid.

6. The applicator of claim 1, wherein said middle section is a longitudinal core extending substantially from the center of said sharp tip section to the center of said base.

7. The applicator of claim 1, wherein said biocompatible ceramic material is in the form of particles.

8. The applicator of claim 1, wherein said augmentation composition further comprises at least one type of skin augmentation material selected from the group consisting of: a biodegradable natural substance, a biodegradable synthetic polymer, a non-biodegradable synthetic polymer, a non-biodegradable natural substance and combinations thereof.

9. The applicator of claim 1, wherein said augmentation composition comprises a biodegradable carrier.

10. The applicator of claim 1, wherein said augmentation composition further comprises a biologically active agent selected from a group consisting of: an enzyme, a drug, a toxin and a combination thereof.

11. The applicator of claim 1, wherein:
    said skeleton is attached to said surface of the substrate intended for being attached to the skin of a subject;
    said skeleton is configured to be fully inserted into the skin;
    the base of the microneedle's skeleton and the sharp tip section are configured to remain devoid of the skin augmentation composition and to prevent delivery of the skin augmentation composition to the epidermis, or to the epidermis and upper dermis; and
    the length of said base section of each of said microneedles is selected in correlation to the location in which said microneedle is configured to be situated at within the treated area.

12. The applicator of claim 1, wherein said skeleton is integrally formed with said surface of the substrate intended for being placed proximal to the skin of a subject.

13. The applicator of claim 1, wherein said skeleton is at least partly inserted into said substrate.

14. The applicator of claim 1, wherein at least part of the surface that is intended for being placed proximal to the skin of the subject is an adhesive surface.

15. A method for filling an undesired fold, wrinkle, line or depressed area in the skin and/or sub-cutis of a subject, comprising placing at the site of said fold, wrinkle, line or depressed area an applicator according to claim 1.

16. A microneedle for administration of a skin augmentation composition to a skin and/or sub-cutis of a subject, the microneedle comprising:
- a skeleton made of a rigid material, the skeleton comprising:
  - a sharp tip section located on one end of said skeleton, the sharp tip section being configured to penetrate the skin of the subject;
  - a base on the opposing end of said skeleton; and
  - a middle section connecting between said sharp tip section and the base; and
- a skin augmentation composition comprising at least one biocompatible ceramic material, wherein the augmentation composition at least partly surrounds the middle section, such that a diameter of said sharp tip section is larger than a diameter of said augmentation composition, and wherein a length of said base is equal or greater than a thickness of an epidermis at a treated area, and wherein the base and the sharp tip section of the microneedle do not comprise the skin augmentation composition.

* * * * *